United States Patent [19]
Malamas et al.

[11] Patent Number: 5,510,360
[45] Date of Patent: Apr. 23, 1996

[54] AZOLIDINEDIONES AS ANTIHYPERGYLCEMIC AGENTS

[75] Inventors: Michael S. Malamas, Jamison, Pa.; Iwan Gunawan, Somerset, N.J.

[73] Assignee: American Home Products Corporation, Madison, N.J.

[21] Appl. No.: 421,111

[22] Filed: Apr. 13, 1995

Related U.S. Application Data

[62] Division of Ser. No. 245,734, May 18, 1994.

[51] Int. Cl.[6] .................. C07D 413/12; C07D 413/14; A61K 31/41
[52] U.S. Cl. ............................. 514/364; 548/132
[58] Field of Search .................... 548/132; 514/364

[56] References Cited

FOREIGN PATENT DOCUMENTS

| | | |
|---|---|---|
| 177353 | 4/1988 | European Pat. Off. . |
| 428312 | 5/1991 | European Pat. Off. . |
| 501892 | 9/1992 | European Pat. Off. . |
| 612743 | 8/1994 | European Pat. Off. . |
| 9203425 | 3/1992 | WIPO . |

*Primary Examiner*—Robert Gerstl
*Attorney, Agent, or Firm*—R. F. Boswell, Jr.

[57] ABSTRACT

This invention relates to novel compounds which have demonstrated oral antihyperglycemic activity in diabetic ob/ob and db/db mice, animal models on non-insulin dependent diabetes mellitus (NIDDM ot Type II diabetes). These compounds have the formula:

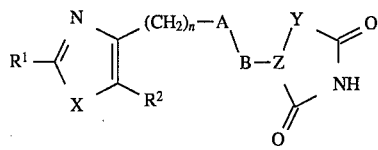

wherein:
X os O or S;
n is 0, 1, or 2;

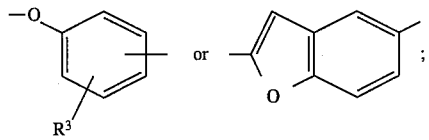

A is

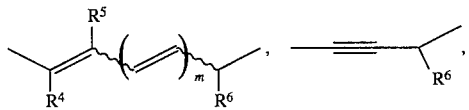

or

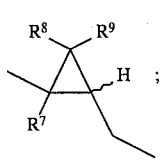

B is
Y is O or S;
Z is N or CH when Y is O and Z is CH when Y is S;
or a pharmaceutically acceptable salt thereof.

9 Claims, No Drawings

AZOLIDINEDIONES AS ANTIHYPERGYLCEMIC AGENTS

This is a division of application Ser. No. 08/245,734, filed May 18, 1994.

This invention relates to novel azolidines of Formula I below which have demonstrated oral antihyperglycemic activity in diabetic db/db and ob/ob mice, animal models of non-insulin dependent diabetes mellitus (NIDDM or Type II diabetes). The Formula I compounds or pharmaceutical compositions thereof are therefore useful in treating hyperglycemia in mammals having non-insulin dependent diabetes mellitus.

BACKGROUND OF THE INVENTION

Diabetes mellitus is a syndrome characterized by abnormal insulin production, increased urinary output and elevated blood glucose levels. There are two major subclasses of diabetes mellitus. One is the insulin-dependent diabetes mellitus (IDDM or Type I), formerly referred to as juvenile onset diabetes since it was evident early in life, and non-insulin dependent diabetes mellitus (NIDDM or Type II), often referred to as maturity-onset diabetes. Exogenous insulin by injection is used clinically to control diabetes but suffers from several drawbacks. Insulin is a protein and thus cannot be taken orally due to digestion and degradation but must be injected. It is not always possible to attain good control of blood sugar levels by insulin administration. Insulin resistance sometimes occurs requiring much higher doses of insulin than normal. Another shortcoming of insulin is that while it may control hormonal abnormalities, it does not always prevent the occurrence of complications such as neuropathy, retinopathy, glomerulosclerosis, or cardiovascular disorders.

Orally effective antihyperglycemic agents are used to reduce blood glucose levels and to reduce damage to the nervous, retinal, renal or vascular systems through mechanisms affecting glucose metabolism. Such agents act in a variety of different mechanisms including inhibition of fatty acid oxidation, α-glycosidase inhibition, antagonism of $\alpha_2$-receptors and inhibition of gluconeogenesis. Two classes of compounds have predominated: the biguanides as represented by phenformin and the sulfonylureas as represented by tolbutamide (Orinase®). A third class of compounds which has shown antihyperglycemic activity are thiazolidinediones of which ciglitazone is the prototype. Ciglitazone suppresses the symptoms of diabetes—hyperglycemia, hypertriglyceridemia and hyperinsulinemia [Diabetes 32, 804–10 (1983)].

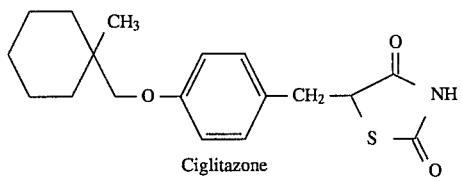
Ciglitazone

Still another class of antihyperglycemic agents are the N-arylalkyl-N-hydroxy ureas and the 2-(arylalkyl)-[1,2,4] oxadiazolidine-3,5-diones. The published PCT patent application WO 92/03425 discloses compounds of the formula:

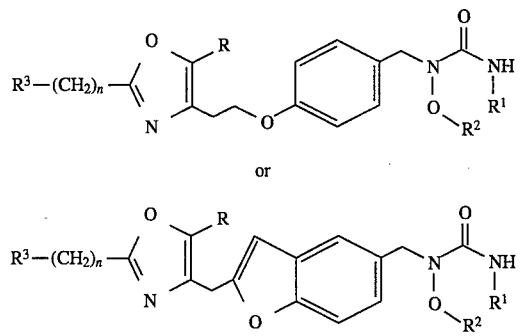

or where $R^1$ and $R^2$ are independently H, $C_1$–$C_9$ alkyl, $C_3$–$C_7$ cycloalkyl, phenyl, etc. or $R^1$ and $R^2$ together are carbonyl, which have utility as hypoglycemic or hypocholesteremic agents.

The hypoglycemic properties of these compounds in ob/ob mice are discussed by Goldstein et al. *J. Med. Chem.* 36, 2238–2240 (1993).

SUMMARY OF THE INVENTION

The novel compounds useful in the treatment of hyperglycemia are represented by the following formula:

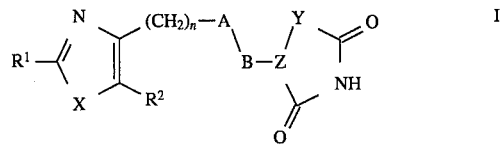

wherein:

$R^1$ is $C_1$–$C_6$ alkyl, $C_3$–$C_8$ cycloalkyl, thienyl, furyl, pyridyl,

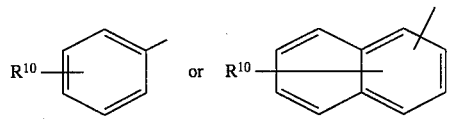

where $R^{10}$ is hydrogen, $C_1$–$C_6$ alkyl, fluorine, chlorine, bromine, iodine, $C_1$–$C_6$ alkyoxy, trifluoroalkyl or trifluoroalkoxy;

$R^2$ is hydrogen or $C_1$–$C_6$ alkyl;

X is O or S;

n is 1 or 2;

A is

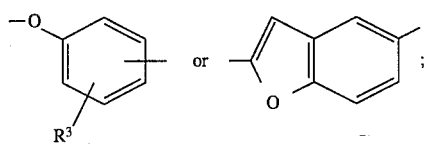

where $R^3$ is hydrogen, $C_1$–$C_6$ alkyl, halogen, $C_1$–$C_6$ alkoxy, trifluoroalkyl or trifluoroalkoxy;

B is

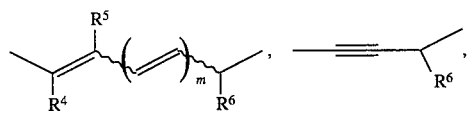

-continued
or

B is where
- $R^4$ is hydrogen, $C_1$–$C_6$ alkyl, allyl, $C_6$–$C_{10}$ aryl, $C_6$–$C_{10}$ aryl-$(CH_2)_{1-6}$—, fluorine, chlorine, bromine, iodine, trimethylsilyl or $C_3$–$C_8$ cycloalkyl;
- $R^5$ is hydrogen, $C_1$–$C_6$ alkyl, $C_6$–$C_{10}$ aryl, or $C_6$–$C_{10}$aryl-$(CH_2)_{1-6}$—;
- m is 0, 1, or 2;
- $R^6$ is hydrogen or $C_1$–$C_6$ alkyl;
- $R^7$ is hydrogen or $C_1$–$C_6$ alkyl;
- $R^8$ and $R^9$ are selected independently from hydrogen, $C_1$–$C_6$ alkyl, fluorine, chlorine, bromine, or iodine;
- Y is O or S;
- Z is N or CH when Y is O and Z is CH when Y is S;

or a pharmaceutically acceptable salt thereof.

The term $C_1$–$C_6$ alkyl means a alkyl group consisting of from one to six carbon atoms which may be a straight or branched chain. The term $C_1$–$C_6$ alkoxy means an O—$C_1$–$C_6$ alkyl group where the $C_1$–$C_6$ group is as defined above. The term $C_6$–$C_{10}$ aryl means phenyl, 1-naphthyl or 2-naphthyl and may be optionally substituted by one to three substituents as listed above according to commercial availability or synthetic means. The term trifluoroalkyl means a group having the formula $CF_3$—$(CH_2)_{0-2}$— and the term trifluoroalkoxy is an O-trifluoroalkyl group where trifluoroalkyl is as defined above.

Compounds of Formula I may be transformed into or isolated as pharmaceutically acceptable salts of alkali metals or alkaline earth metals, such as a sodium, potassium, lithium or calcium salt. It will also be recognized by those skilled in the art that the active compound or salt thereof may be isolated as a solvate or hydrate which is considered to have the pharmacological properties of the active compound.

The preferred compounds are those of Formula Ia below

Ia where
- $R^{10}$ is hydrogen, $C_1$–$C_6$ alkyl, fluorine, chlorine, bromine, iodine, $C_1$–$C_6$ alkoxy, trifluoroalkyl or trifluoroalkoxy;
- n is 1 or 2;
- A is or B is or where
- m is 0, 1 or 2;
- $R^4$, $R^5$, $R^6$, and $R^7$ are independently hydrogen or $C_1$–$C_6$ alkyl;
- Y is O or S;
- Z is N or CH when Y is O and Z is CH when Y is S;

or a pharmaceutically acceptable salt thereof.

The most preferred compounds of this invention are those of Formula Ib

Ib wherein:
- $R^{10}$ is hydrogen, $CF_3$—, $CF_3O$—, $CF_3CH_2O$— or Cl—;
- n is 1 or 2;
- A is or B is or wherein
- m is 0 or 1;
- $R^4$, $R^5$, $R^6$, and $R^7$ are independently hydrogen, methyl or ethyl;
- Y is O or S;
- Z is N or CH when Y is O and Z is CH when Y is S;

or a pharmaceutically acceptable salt thereof.

The most preferred compounds of the invention are the following:

(E)-2-(3-{3-[5-methyl-2-(4-trifluoromethyl-phenyl-oxazol-4-ylmethoxy]-phenyl}-pent-2-enyl)-[1,2,4]-oxadiazolidine-3,5-dione, (Z)-2-(3-{3-[5-methyl-2-(4-trifluoromethyl-phenyl)-oxazol-4-ylmethoxy]-phenyl}-pent-2-enyl)-[1,2,4]oxadiazolidine-3,5dione, 2-(3-{3-[5-methyl-2-(4-trifluoromethyl-phenyl)-oxazol-4-ylmethyl]-phenyl}-but-2-enyl)-[1,2,4]oxadiazolidine-3,5-dione, (E)-2-(3-{3-[5-methyl-2-(4-trifluoromethoxy-phenyl)-oxazol-4-ylmethoxy]-phenyl}-but-2-enyl)-[1,2,4,]oxadiazolidine-3,5-dione, (E)-2-(3-}3-[5-methyl-2-(4-trifluoro-ethoxy-phenyl)-oxazol-4-ylmethoxy]-phenyl}-but-2-enyl)-[1,2,4]oxadiazolidine-3,5-dione, (E)-2-{3-[3-(5-methyl-2-phenyl-oxazol-4-ylmethoxy]-phenyl[-but-2-enyl}-[1,2,4]oxadiazolidine-3,5-dione, (Z)-2-{3-[3-(5-methyl-2-phenyl-oxazol-4-ylmethoxy]-phenyl]-but-2-enyl}-[1,2,4]oxadiazolidine-3,5-dione, (E)-2-{3-[3-[2-(5-methyl-2-phenyl-oxazol-4-yl)-ethoxy]-phenyl}-but-2-enyl)-[1,2,4,]oxadiazolidine-3,5-dione, 2-{3-[3-(5-methyl-2-phenyl-oxazol-4-ylmethoxy]-benzofuran-5-yl]-but-2-enyl}-[1,2,4]oxadiazolidine-3,5-dione, (E)-2-(2-methyl-3-{4-[5-methyl-2-(4-trifluoromethyl-phenyl)-oxazol-4-ylmethoxy]-phenyl}-allyl)-[1,2,4]oxadiazolidine-3,5-dione, (E)-2-(2-ethyl-3-{3-[5-methyl-2-(4-trifluoromethyl-phenyl)-oxazol-4-ylmethoxy]-phenyl}-allyl)-[1,2,4]oxadiazolidine-3,5-dione, (E)-2-(1-methyl-3-{3-[5-methyl-2-(4-trifluoromethyl-phenyl)-oxazol-4-ylmethoxy]-phenyl}-allyl)-[1,2,4]oxadiazolidine-3,5-dione, (E)-2-(3-{3-[2-(4-chloro-phenyl)-5-methyl-oxazol-4-ylmethoxy]-phenyl}-1-methyl-allyl)-[1,2,4]oxadiazolidine-3,5-dione, (E)-2-(2-methyl-3-{3-[5-methyl- 2-(4-trifluoromethyl-phenyl)-oxazol-4-ylmethoxy]-phenyl}-but-2-enyl)-[1,2,4]oxadiazolidine-3,5-dione, (Z)-2-(2-methyl-3-{3-[5-methyl-2-(4-trifluoromethyl-phenyl)-oxazol-4-ylmethoxy]-phenyl}-but-2-enyl)-[1,2,4]oxadiazolidine-3,5-dione, (E)-2-(1-methyl-3-{3-[5-methyl-2-(4-trifluoromethyl-phenyl)-oxazol-4-ylmethoxy]-phenyl}-but-2-enyl)-[1,2,4]oxadiazolidine-3,5-dione, 2-[3-(4-{4-[5-methyl-2-(4-trifluoromethyl-phenyl)-oxazol-4-ylmethoxy]-phenyl}- allyl) -[1,2,4]oxadiazolidine-3,5-dione, (E)-2-(2{3-[5-methyl-2-(4-trifluoromethyl-phenyl)-oxazol-4-ylmethoxy]-phenyl}-cyclopropylmethyl)-[1,2,4]oxadiazolidine-3,5-dione, (E)-2-(2-methyl-2-{3-[5-methyl- 2-(4-trifluoromethyl-phenyl)-oxazol-4-ylmethoxy]-phenyl}-cyclopropylmethyl)-[1,2,4]oxadiazolidine-3,5-dione, (E,E)-2-{5-[3-(5-methyl-2-phenyl -oxazol-4-ylmethoxy]-phenyl}-hexa-2,4-dienyl)-[1,2,4]oxadiazolidine-3,5-dione, (Z,E)-2-{5-[3-(5-methyl-2-phenyl-oxazol -4-ylmethoxyl]-phenyl}-hexa-2,4-dienyl)-[1,2,4]oxadiazolidine-3,5-dione, 2-[3-(4-{2-[5-methyl-2-(4- trifluoromethyl-phenyl-oxazol-4-yl]-ethoxy}-phenyl)-propyl-2-ynyl)-[1,2,4]oxadiazolidine-3,5-dione, 2-{1-methyl-3-[3-(5-methyl-2-phenyl -oxazol-4-ylmethoxy)-phenyl]-propyl-2-ynyl}-[1,2,4]oxadiazolidine-3,5-dione, (E)-5-{3-[3-(5-methyl-2-phenyl-oxazol -4-ylmethyl]-phenyl]-but-2-enyl}-oxazolidine-2,4-dione, (E)-5-[3-(3-{5-methyl-2-[4-(2,2,2,-trifluoro-ethoxy)-phenyl]-oxazol-4-ylmethoxy}-phenyl) -but-2-enyl]-oxazolidine-2,4-dione, (E)-5-(3-{3-[5-methyl-2-(trifluoromethoxy-phenyl)-oxazol-4-ylmethoxy]-phenyl}-but-2-enyl)-oxazolidine-2,4-dione, (E)-5-(3-{3-[2-(5-methyl-2-phenyl) -oxazol-4-yl)-ethoxy]-phenyl}-but-2-enyl)-oxazolidine-2,4-dione, (E)-5-{3-[3-(5-methyl-2-phenyl)-oxazol -4-ylmethoxy]-phenyl}-but-2-enyl)-thiazolidine-2,4-dione, and (E)-5-(3-{3-[5-methyl-2-(4-trifluoromethoxy-phenyl)-oxazol-4-ylmethoxy]-phenyl}-but-2-enyl)-thiazolidine-2,4-dione.

DETAILED DESCRIPTION OF THE INVENTION

The invention compounds of Formula I may be prepared from intermediates of the formula II below wherein the variables n, $R^1$, $R^2$, X, A and B are as previously defined.

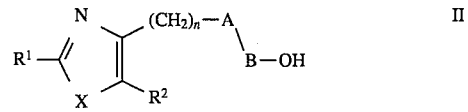

Oxadiazolidinediones of Formula I are prepared from a Formula II intermediate by first converting to a hydroxylamine followed by reaction with N-(chlorocarbonyl) isocyanate or by converting the Formula II alcohol to a N-hydroxyurea which is reacted with methyl chloroformate to give a Formula I oxadiazolidinedione. The Formula I oxazolidinediones and thiazolidinediones are prepared by converting the intermediate of Formula II to the halide of Formula III below followed by reaction with 2,4-oxazolidinedione or 2,4-thiazolidinedione.

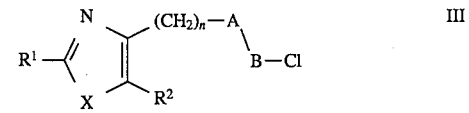

These synthetic transformations are more fully described in the following reaction schemes I–XIL Scheme I outlines the synthesis of a Formula II intermediate where A is phenyl and B is an olefinic linking group as shown under Formula I.

Scheme I
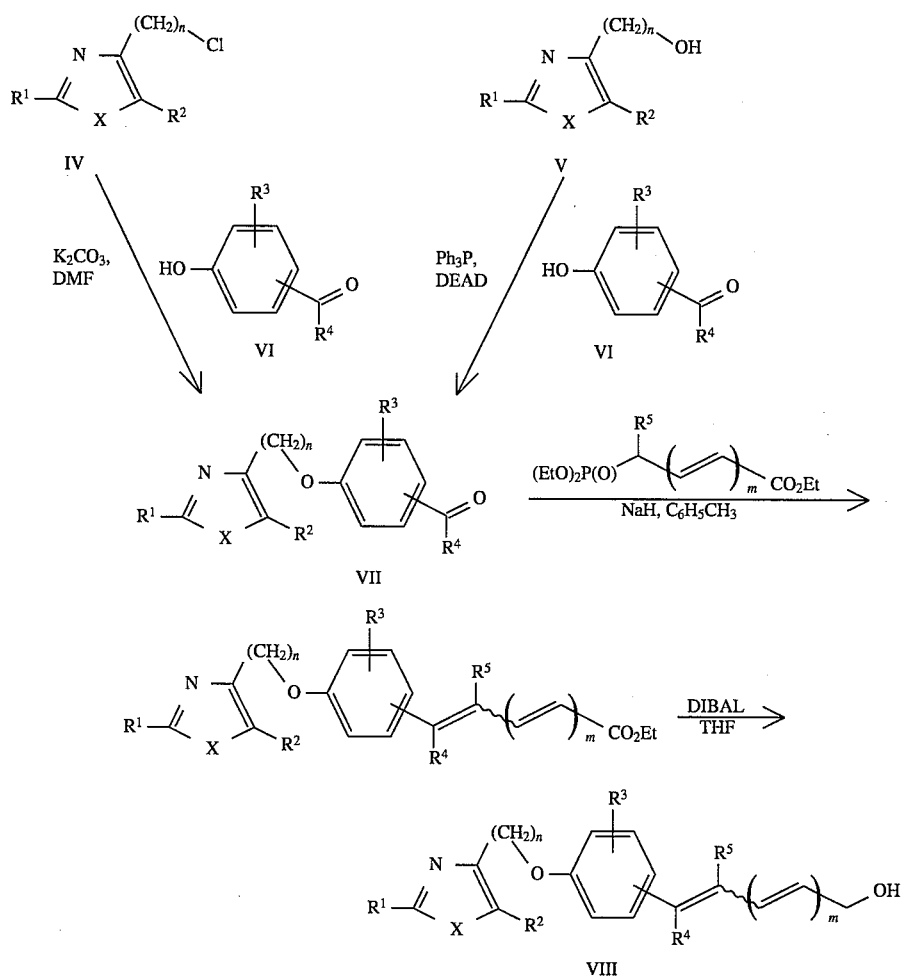
The terms $R^1$–$R^5$, X, n, and m are as defined previously.
Scheme II illustrates the synthetic sequence for preparing a Formula I compound from the intermediate VIII.
Scheme II
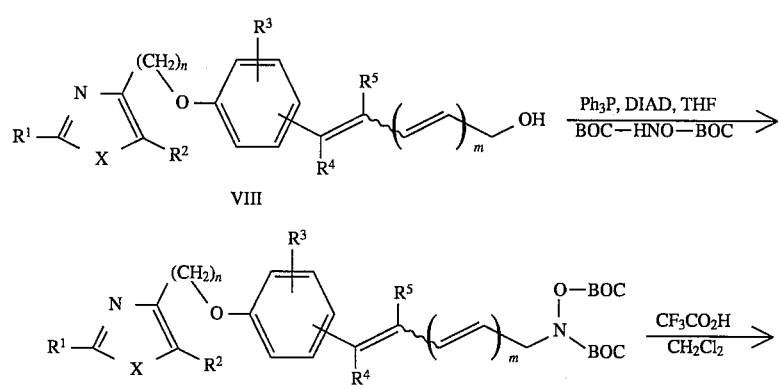

-continued
Scheme II
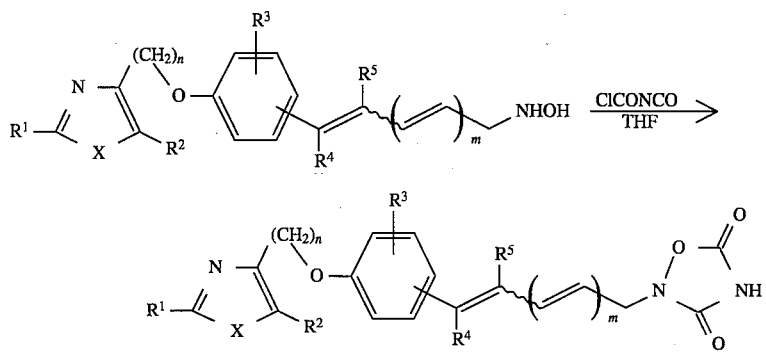
The terms $R^1$–$R^5$, X, n, and m are as defined previously.
When $R^4$ is halogen the compounds of the present invention can be prepared according to Scheme III.
When $R^6$ is alkyl the compounds of the present invention can be prepared according to Scheme IV
Scheme III
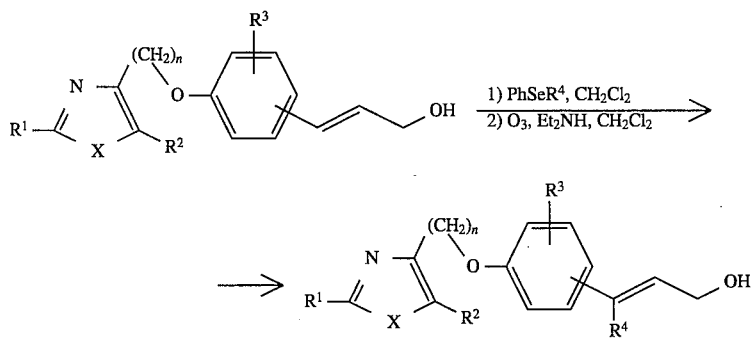
wherein $R^1$, $R^2$, $R^3$, X, and n are as defined above; $R^4$ is halogen.
Scheme IV
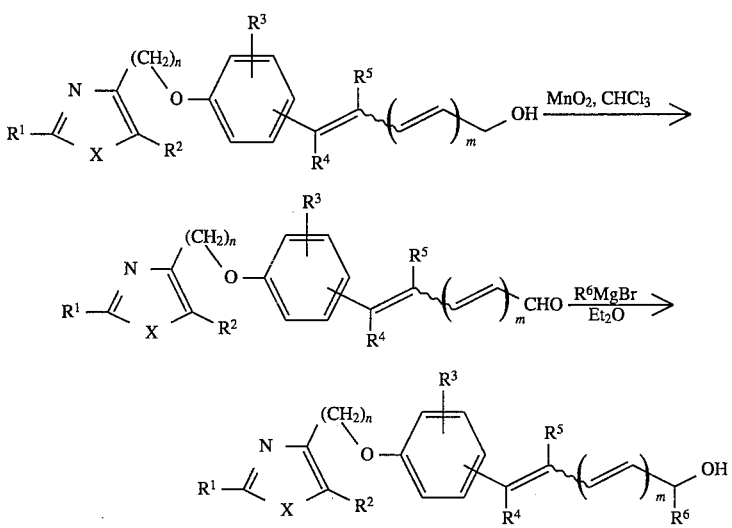

wherein $R^1$, $R^2$, $R^3$, $R^4$, $R^5$, $R^6$, X, n and m are as defined above.

Scheme V outlines the synthesis of an intermediate where B is cyclopropylmethyl from an intermediate of Formula VIII where m is 0.

Scheme V

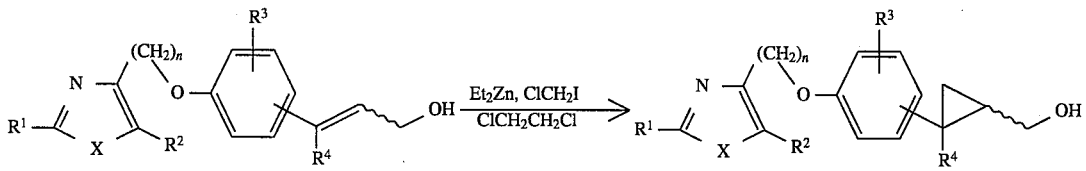

wherein $R^1$, $R^2$, $R^3$, X, and n are as defined above; $R^4$ is hydrogen, alkyl, aryl, aralkyl, cycloalkyl.

Scheme VI outlines the synthesis of a Formula II intermediate where B is propynyl.

Scheme VI

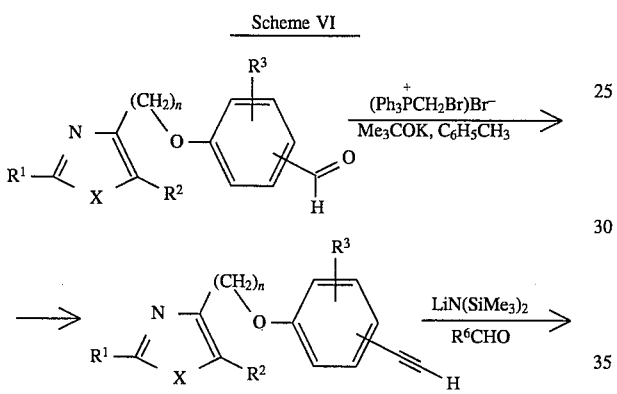

-continued
Scheme VI

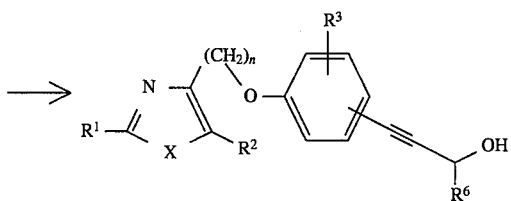

wherein $R^1$, $R^2$, $R^3$, $R^6$, X, and n are as defined above

Scheme VII outlines the reactions used to prepare Formula I compounds where Z is CH and Y is O or S from an intermediate of Formula VIII.

Scheme VII

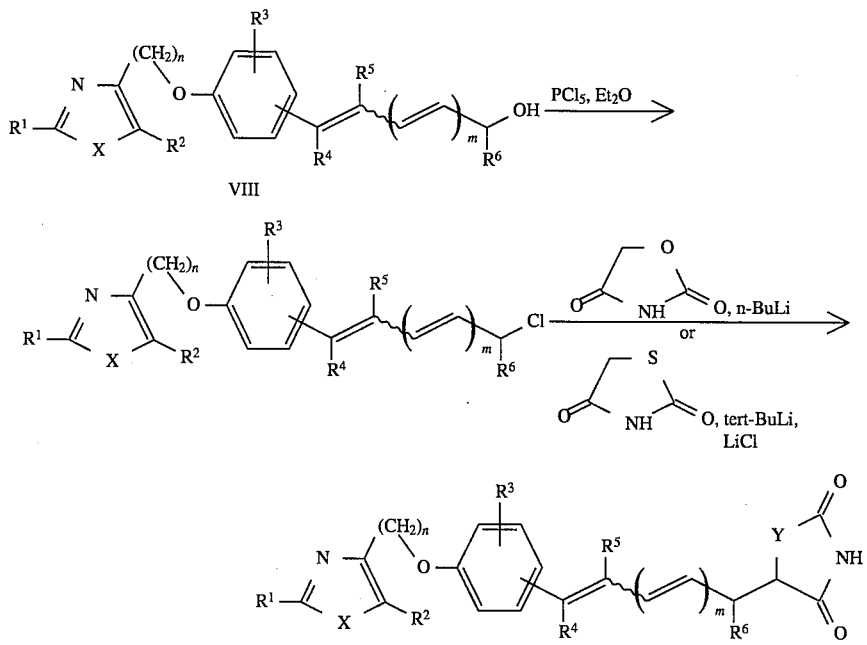

wherein $R^1$, $R^2$, $R^3$, $R^5$, $R^6$, X, n and m are as defined above; $R^4$ is hydrogen, alkyl, allyl, aryl, aralkyl, trimethylsilyl, cycloalkyl; Y is O or S.

Preparation of a Formula I compound where A is benzofuran-2,5-diyl, Y is O and Z is N is shown in Scheme VIII.

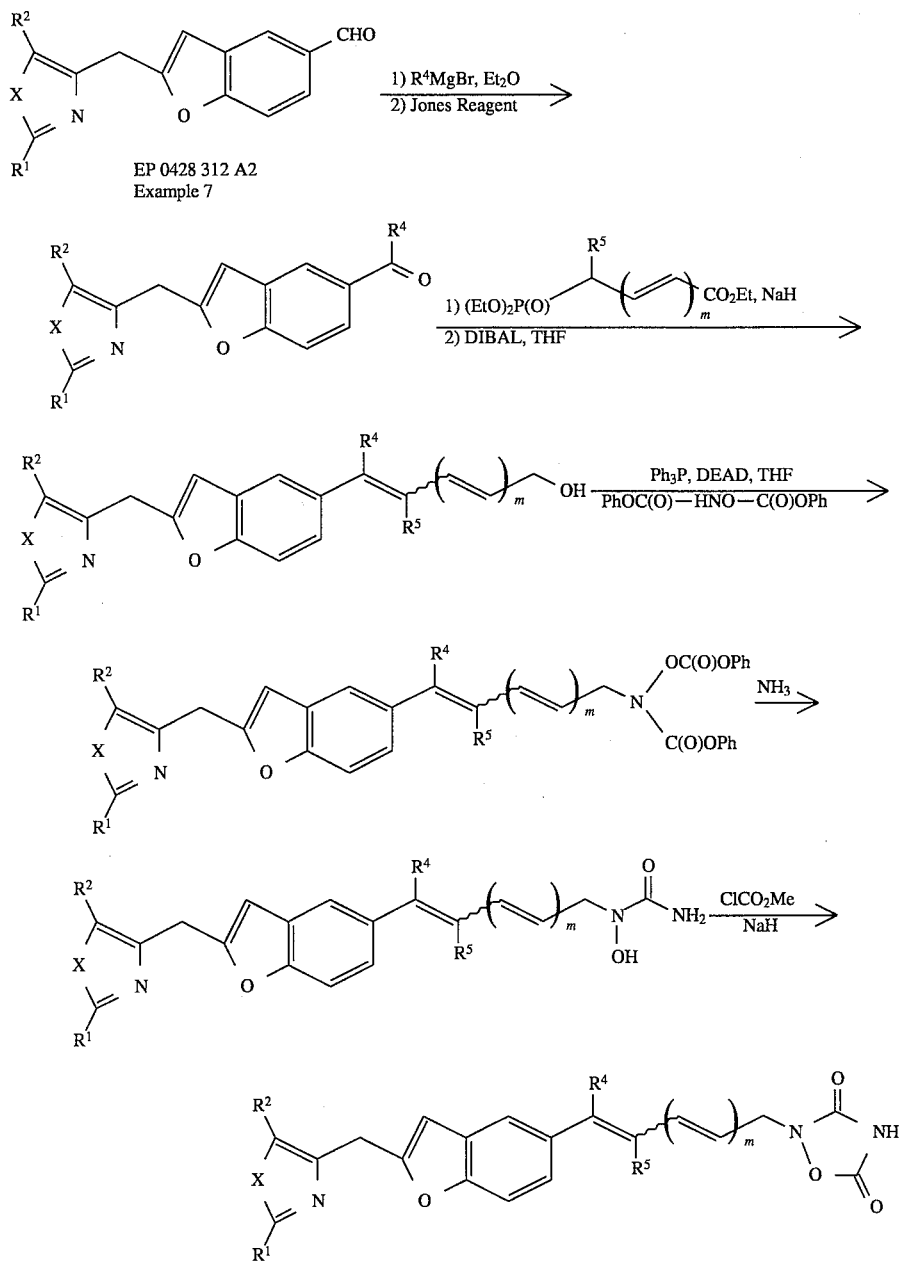

wherein $R^1$, $R^2$, $R^5$, x and m are as defined above; $R^4$ is hydrogen, alkyl, allyl, aryl, aralkyl, trimethylsilyl, cycloalkyl.

The starting heterocyclic intermediates of the formula V can be prepared according to standard literature procedures. For example, 4-(1'-hydroxyethyl)-5-$R^2$-2-phenyloxazoles and thiazoles where $R^2$ is hydrogen or $C_1$–$C_6$ alkyl can be prepared according to Scheme IX (European Patent EP 0177353A2).

Scheme IX

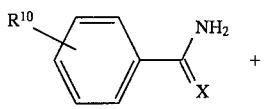

-continued
Scheme IX

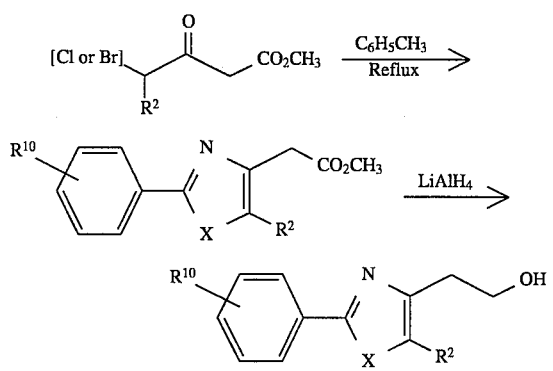

The starting heterocyclic intermediates of the formula IV can be prepared by known methods conventional in the art (Heterocyclic Compounds 34, 1979 and Heterocyclic Compounds 45, 1986). The 2-phenyl-4-chloromethyl-5-methyloxazoles can be prepared according to the reaction sequence shown in Scheme X.

Scheme X

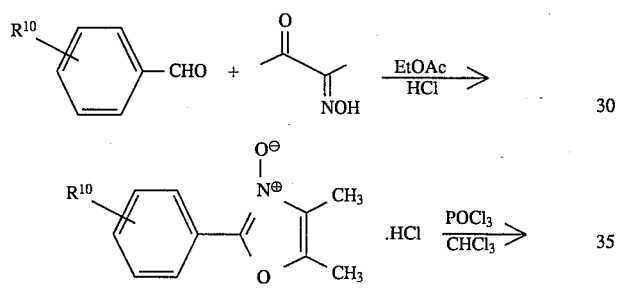

-continued
Scheme X

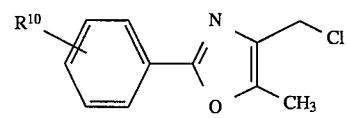

The intermediate 4-chloromethyl-2-phenyloxazoles or thiazoles can be prepared according to the reaction shown in Scheme XI.

Scheme XI

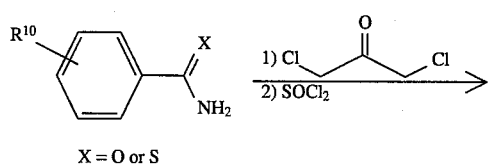

$X = O \text{ or } S$

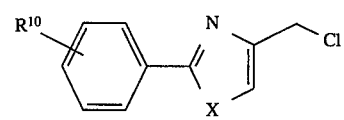

Intermediate of the formula VII can be prepared either from the commercially available phenols of formula IX or according to the synthetic Scheme XII.

Scheme XII

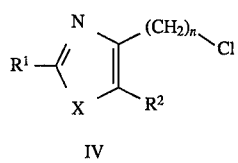
IV

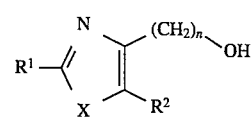
V

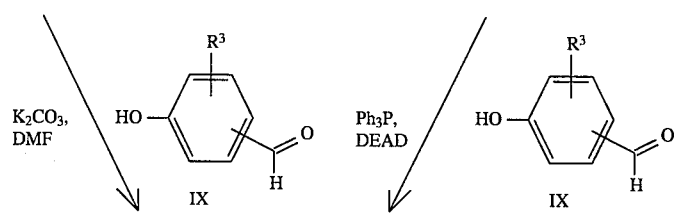

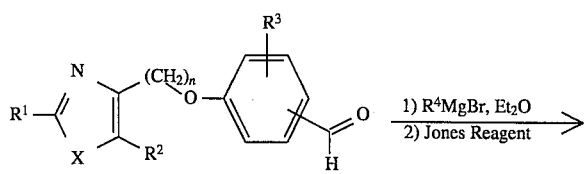

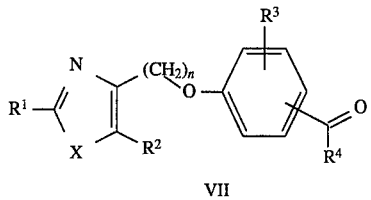

VII

The following examples are included for illustrative purposes and are not intended to limit the disclosure of this invention in any way. The reagents, intermediates, or chemicals used herein are either commercially available or can be readily synthesized using standard laboratory procedures known to those skilled in the art.

EXAMPLE 1

(E)-2-(3-{3-[5-methyl-2-(4-trifluoromethyl-phenyl)-oxazol-4-ylmethoxyl-phenyl}-pent-2-enyl)-[1,2,4]oxadiazolidine-3,5-dione

Step a)
3-[5-methyl-2-(-4-trifluoromethyl-phenyl)-oxazol-4-ylmethoxy)-benzaldehyde A mixture of 4-chloromethyl-5-methyl-2-(4-trifluoromethyl-phenyl)-oxazole (5.25 g, 19.1 mmol), 3-hydroxylbenzaldehyde (2.33 g, 19.1 mmol), potassium carbonate (3.77 g, 27.3 mmol) and dimethylformamide (50 mL) was stirred at 80° C. for 3 hours. The mixture was then poured into $H_2O$, acidified with HCl (2N) and extracted with EtOAc. The organic extracts were dried over $MgSO_4$. Evaporation and crystallization from ethyl ether/hexane, gave a yellow solid (4.47 g, 65% yield, m.p. 104°–105° C.).

Analysis for: $C_{19}H_{14}F_3NO_3$ Calc'd: C, 63.16; H, 3.91; N, 3.88 Found: C, 62.84; H, 3.97; N, 3.87

Step b)
1-{3-[5-methyl-2-(4-trifluoromethyl-phenyl)-oxazol-4-ylmethoxy]-phenyl}-propan-1-one Ethylmagnesium bromide (11.1 mL, 33.24 mmol) was added dropwise in to a cold (0° C.) solution of 3-[5-methyl-2-(-4-ylmethoxy)-benzaldehyde (12.0 g, 33.24 mmol) and THF (50 mL). After stirring for 30 minutes the reaction mixture was quenched with aqueous $NH_4Cl$, poured into water, acidified with HCl (2N) and extracted with EtOAc. The organic extracts were dried over $MgSO_4$. Evaporation gave a yellowish oil (13.0 g), which was dissolved in acetone (200 mL). The mixture was cooled to 5° C. and freshly prepared Jones' Reagent (40 mL) was added dropwise. After the addition, the mixture was stirred for 30 minutes, poured into water and extracted with EtOAc. The organic extracts were dried over $MgSO_4$. Evaporation and crystallization from ethyl ether/hexane (after cooling to 0° C.), gave a white solid (9.6 g, 74% yield, m.p. 73°–74° C.).

Analysis for: $C_{38}H_{36}N_2O_9$ Calc'd: C, 64.78; H, 4.66; N, 3.60 Found: C, 64.63; H, 4.60; N, 3.91

Step c)
(E)-3-{3-[5-Methyl-2-(4-trifluoromethyl-phenyl)-oxazol-4-ylmethoxyl-phenyl}-pent-acid ethyl ester Triethylphosphonoacetate (8.67 ml, 43.1 mmol) was added dropwise in to a cold (0° C.) suspension of sodium hydride (1.24 g, 41.5 mmol) and toluene (200 ml). After the addition, the mixture was stirred for 1 hour, and then 1-{3-[5-methyl-2-(4-trifluoromethyl-phenyl)-oxazol-4-yl-methoxy]-phenyl}-propan-1-one (8.5 g, 21.85 mmol) in THF (20 ml) was added dropwise. The reaction mixture was stirred at room temperature for 24 hours, poured into water, acidified with HCl (2N), and extracted with EtOAc. The organic extracts were dried over $MgSO_4$. Evaporation and purification by flash chromatography on silica gel (hexane/EtOAc 8/1) gave the trans-isomer (white solid, 5.5 g, 55% yield, m.p. 85°–86° C.), and the cis-isomer (clear oil, 2.8 g 28% yield).

a) Analysis for: $C_{25}H_{24}F_3NO_4$ (trans-isomer) Calc'd: C, 65.35; H, 5.27; N, 3.05 Found: C, 65.25; H, 5.42; N, 3.01 b) Analysis for: $C_{25}H_{24}F_3NO_4$ (cis-isomer) Calc'd: C, 65.35; H, 5.27; N, 3.05 Found: C, 65.11; H, 5.31; N, 3.00

Step d)
(E)-3-{3-[5-Methyl-2-(4-trifluoromethyl-phenyl)-oxazol-4-ylmethoxyl-phenyl}-pent-2-en-1-ol Di-isobutyl aluminum hydride (1.0M in THF, 25.05 ml, 25.05 mmol) was added dropwise in to a cold (−50° C.) solution of (E)-3-{3-[5-methyl-2-(4-trifluoromethyl-phenyl)-oxazol-4-ylmethoxyl]-phenyl}-pent-2enoic acid ethyl ester (4.6 g, 10 mmol) in THF (100 ml) and ethyl ether (100 mL). The reaction was warmed to 0° C. and stirred for 1 hour. The reaction mixture was quenched with acetone (dropwise addition), methanol, poured into water, acidified with HCl (2N), and extracted with EtOAc. The organic extracts were dried over $MgSO_4$. Evaporation and purification by flash chromatography on silica gel (hexane/EtOAc 3/1), gave a clear oil (3.8 g, 91% yield).

Analysis for: $C_{23}H_{22}F_3NO_3$ Calc'd: C, 66.18; H, 5.31; N, 3.36 Found: C, 65.88; H, 5.41; N, 3.26

Step e)
(E)-N-tert-Butoxycarbonyloxy-(3-{3-[5-methyl-2-(4-trifluoromethyl-phenyl)-oxazol-4-ylmethoxy]-phenyl}-pent-2-enyl)-carbamic acid tert-butyl ester Diisopropylazodicarboxylate (1.98 ml, 10.07 mmol) in THF (15 ml) was added dropwise n to a cold (−20° C.) solution of (E)-3-{3-[5-methyl-2-(4-trifluoromethyl-phenyl)-oxazol-4 4-ylmethoxy]-phenyl}-pent-2-en-1-ol (3.5 g, 8.39 mmol) in THF (30 ml), triphenylphosphine (2.64 g, 10.07 mmol) and tert-butyl N-(tert-butoxy-carbonyloxy) carbamate (2.35 g, 10.07 mmol). After the addition, the mixture was stirred for 1 hour, poured into water, and extracted with EtOAc. The organic extracts were dried over $MgSO_4$. Evaporation and purification by flash chromatography on silica gel (hexane/EtOAc 7/1) gave a clear oil (5.1 g, 96% yield).

Analysis for: $C_{33}H_{39}F_3N_2O_7 \times 0.5\ H_2O$ Calc'd: C, 61.77; H, 6.24; N, 4.37 Found: C, 61.58; H, 6.46; N, 4.60

19

Step f)
(E)-N-(3-{3-[5-Methyl-2-(4-trifluoromethyl-phenyl)-oxazol-4-ylmethoxy]-pent-2-enyl)-hydroxylamine A mixture of (E)-N-tert-butoxycarbonyloxy-3-(3-{3-[5-methyl-2-(4-trifluoromethyl-phenyl)-oxazol-4-ylmethoxy]-phenyl}-pentyl-2-enyl)-carbamic acid tert-butyl ester (5.0 g, 7.9 mmol), $CH_2Cl_2$ (100 ml), and trifluoroacetic acid (10 ml) was stirred at room temperature for 8 h. The volatiles were removed in vacuo, and the residue taken in ethylether/water. It was basified to pH=9-10 with NaOH (2N), and the organic layer separated and washed with water and brine. The organic extracts were dried over $MgSO_4$. Evaporation and purification by flash chromatography on silica gel (hexane/EtOAc 1/1, and MeOH/EtOAc 1/10), gave a clear oil (3.0 g, 88% yield).

Analysis for: $C_{23}H_{23}F_3N_2O_3$ Calc'd: C, 63.88; H, 5.36; N, 6.48 Found: C, 63.63; H, 5.27; N, 6.48

Step g)
(E)-2-(3-{3-[5-methyl-2-(4-trifluoromethyl-phenyl)-oxazol-4-ylmethoxy]-phenyl}-pent-2-enyl)-[1,2,4]oxadiazolidine-3.5-dione N-(Chlorocarbonyl)isocyanate (0.37 ml, 4.63 mmol) was added dropwise to a cold (–5° C.) mixture of (E)-N-(3-{3-[5-methyl-2-(4-trifluoromethyl-phenyl)-oxazol-4-ylmethoxy]-phenyl}-pent-2-enyl)-hydroxylamine (2.0 g, 4.63 mmol) in THF (20 ml). The mixture was stirred for 30 minutes, then poured into HCl (1N) and extracted with EtOAc. The organic extracts were dried over $MgSO_4$. Evaporation and purification by flash chromatography on acid washed (5% $H_3PO_4$/MeOH) silica gel (hexane/EtOAc 3/1) gave a white solid (1.48 g, 64% yield, mp 66–67° C.).

Analysis for: $C_{25}H_{22}F_3N_3O_5$ Calc'd: C, 59.88; H, 4.42; N, 8.38 Found: C, 59.83; H, 4.37; N, 8.28

EXAMPLE 2

(E)-2-(3-{3-[5-methyl-2-(4-trifluoromethyl-phenyl)-oxazol-4-ylmethoxy]-phenyl}-pent-2-enyl)-[1,2,4]oxadiazolidine-3,5-dione

Step a)
(Z)-3-{3-[5-Methyl-2-(4-trifluoromethyl-phenyl)-oxazole-4-ylmethoxyl]-phenyl}-pent-2-en-1-ol Di-isobutyl aluminum hydride (1.0M in THF, 10.89 ml, 10.89 mmol) was added dropwise in to a cold (–50° C.) solution of (Z)-3-{3-[5-methyl-2-(4-trifluoromethyl-phenyl)-oxazol-4-ylmethoxy]-phenyl}-pent-2-enoic acid ethyl ester (2.0 g, 4.35 mmol) in THF (30 ml) and ethyl ether (30 mL). The reaction was warmed to 0° C. and stirred for 1 hour. The reaction mixture was quenched with acetone (dropwise addition), methanol, poured into water, acidified with HCl (2N), and extracted with EtOAc. The organic extracts were dried over $MgSO_4$. Evaporation and purification by flash chromatography on silica gel (hexane/EtOAc 3/1), gave a white solid (1.65 g, 91% yield, m.p. 88°–89° C.).

Analysis for: $C_{23}H_{22}F_3NO_3$ Calc'd: C, 66.18, H, 5.31; N, 3.36 Found: C, 65.85; H, 5.12; N, 3.15

20

Step b)
(Z)-N-(3-{3-[5-Methyl-2-(4-trifluoromethyl-phenyl)-oxazol-4-ylmethoxy]-phenyl}-pent-2-enyl)-hydroxylamine Diisopropylazodicarboxylate (0.68 ml, 3.45 mmol) in THF (10 ml) was added dropwise n to a cold (–20° C.) solution of (Z)-3-{3-[5-methyl-2-(4-trifluoromethyl-phenyl)-oxazol-4-ylmethoxy]-phenyl}-pent-2en-1-ol (1.2 g, 2.87 mmol), THF (20 ml), triphenylphosphine (0.9 g, 3.45 mmol) and tert-butyl N-(tert-butoxy-carbonyloxy) carbamate (0.8 g, 3.45 mmol). After the addition, the mixture was stirred for 1 hour, poured into water, and extracted with EtOAc. Evaporation gave a yellowish oil (1.7 g), which was dissolved in $CH_2Cl2$ (30 mL), and treated with trifluoroacetic acid (3.0 mL). After stirring at room temperature for 8 hours, the volatiles were removed in vacuo, and the residue taken in ethylether/water. It was basified to pH=9–10 with NaOH (2N), and the organic layer separated and washed with water and brine. The organic extracts were dried over $MgSO_4$. Evaporation and purification by flash chromatography on silica gel (hexane/EtOAc 1/1, and MeOH/EtOAc 1/10), gave a white solid (3.0 g, 82% yield, m.p. 72–73° C.).

Analysis for: $C_{23}H_{23}F_3N_2O_3$ Calc'd: C, 63.88; H, 5.36; N, 6.48 Found: C, 63.74; H, 5.34; N, 6.26

Step c)
(Z)-2-(3-{3-[5-methyl-2-(4-trifluoromethyl-phenyl)-oxazol-4-ylmethoxy]-phenyl}-pent-2-enyl)-[1,2,4]oxadiazolidine-3.5-dione N-(Chlorocarbonyl)isocyanate (0.12 ml, 1.5 mmol) was added dropwise to a cold (–5° C.) mixture of (Z)-N-(3-{3-[5-methyl-2-(4-trifluoromethyl-phenyl)-oxazol-4-ylmethoxy]-phenyl}-pent-2-enyl)-hydroxylamine (0.65 g, 1.5 mmol) in THF (10 ml). The mixture was stirred for 30 minutes, then poured into HCl (1N) and extracted with EtOAc. The organic extracts were dried over $MgSO_4$. Evaporation and purification by flash chromatography on acid washed (5% $H_3PO_4$/MeOH) silica gel (hexane/EtOAc 2/1) gave a white solid (0.48 g, 64% yield, mp 126°–127° C.).

Analysis for: $C_{25}H_{22}F_3N_3O_5$ Calc'd: C, 59.88; H, 4.42; N, 8.38 Found: C, 60.03; H, 4.55; N, 8.03

EXAMPLE 3

(E)-2-(3-{3-[5-methyl-2-(4-trifluoromethyl-phenyl)-oxazol-4-ylmethyl]-phenyl}-but-2-enyl)-[1,2,4]oxadiazolidine-3.5-dione

Step a)
4.5-Dimethyl-2-(4-trifluoromethyl-phenyl)-oxazole N-oxide hydrochloride HCl gas (21.2 g, 58.1 mmol) was bubbled via syringe into 0° C. solution of 4-trifluoromethylbenzaldehyde (50 g, 28.7 mmol), 2,3-butanedione monoxime (26.40 g, 26.1 mmol), and EtOAc (105 ml). The reaction was stirred at 5° C. for 3 h. Ice cold ether (575 ml) was then added, and the resultant precipitate was filtered, washed with ether, and dried at 25° C. for 16 h to give the product as a white solid (54.79 g 71% yield, mp 149°–159° C.

Analysis for: $C_{12}H_{11}ClF_3NO_2$ Calc'd: C, 49.08; H, 3.77; N, 4.77 Found: C, 49.48; H, 3.81; N, 4.88

Step b)
4-Chloromethyl-5-methyl-2-(4-trifluoromethyl-phenyl)-oxazole

In to a 5° C. solution of 4,5-dimethyl-2-(4-trifluoromethyl-phenyl)-oxazole N-oxide hydrochloride (113.71 g, 387.5 mmol) in CHCl$_3$ (560 ml), was added phosphorus oxychloride (39.4 ml, 422.4 mmol) in CHCl$_3$, dropwise over 15 min. The reaction was refluxed for 2.5 h, then cooled to 5° C., poured into ice water, and basified with NaOH (1N). The organic layer was dried over MgSO$_4$. Evaporation and recrystallization from ether/hexane, gave a yellow solid (30.0 g, 28% yield, mp 84°–85° C.).

Analysis for: C$_{12}$H$_9$ClF$_3$NO Calc'd: C, 52.29; H, 3.29; N, 5.08 Found: C, 52.54; H, 3.20; N, 4.92

Step c)
1-{3-[5-methyl-2-(4-trifluoromethyl-phenyl)-oxazol-4-ylmethoxy]-phenyl}-ethanone A mixture of 4-chloromethyl-5-methyl-2-(4-trifluoromethyl-phenyl)-oxazole (24.3 g, 88.2 mmol), 3-hydroxyacetophenone (10.0 g, 73.5 mmol), and potassium carbonate (13.2 g, 95.6 mmol), was stirred at 70° C. for 16 h. The reaction was poured into water, acidified with HCl (1N), and extracted with EtOAc. The organic extracts were dried over MgSO$_4$. Evaporation and purification by flash chromatography on silica gel (hexane/EtOAc 9/1), gave an off-white solid (20.14 g, 60% yield, mp 90°–91° C.).

Analysis for: C$_{20}$H$_{16}$F$_3$NO$_3$ Calc'd: C, 63.99; H, 4.29; N, 3.73 Found: C, 63.86; H, 4.30; N, 3.64

Step d)
(E)-3-{3-[5-methyl-2-(4-trifluoromethyl-phenyl)-oxazol-4-ylmethoxy]-phenyl}-but-2-enoic acid ethyl ester In to a 0° C. mixture of sodium hydride (4.27 g, 142.6 mmol) and toluene (500 ml), was added triethylphosphonoacetate (29.79 ml, 150.1 mmol) via syringe. The reaction was stirred for 1 hour, and then 1-{3-[5-methyl-2-(4-trifluoromethyl-phenyl)-oxazol-4-ylmethoxy]-phenyl}-ethanone (28.15 g, 75.1 mmol) in THF (150 ml) was added dropwise. The reaction mixture was stirred at room temperature for 16 h, poured into water, acidified with HCl (2N), and extracted with EtOAc. The organic extracts were dried over MgSO$_4$. Evaporation and purification by flash chromatography on silica gel (hexane/EtOAc 20/1) gave a white solid (24.42 g, 73% yield, mp 91°–92° C.).

Analysis for: C$_{24}$H$_{23}$F$_3$NO$_4$ Calc'd: C, 64.57; H, 5.19; N, 3.14 Found: C, 64.81; H, 5.01; N, 3.13

Step e)
(E)-3-{3-[5-methyl-2-(4-trifluoromethyl-phenyl)-oxazol-4-ylmethoxyl]-phenyl}-but-2-en-1-ol Di-isobutyl aluminum hydride (1.0M in THF) (219.2 ml, 219.2 mmol) was added, by syringe, to a –25° C. solution of 3-{3-[5-methyl-2-(4-trifluoromethyl-phenyl)-oxazol-4-ylmethoxy]-phenyl}-but-2-enoic acid ethyl ester (24.42 g, 54.8 mmol) in THF (300 ml). The reaction was warmed to 0° C. and stirred for 1.5 h. It was poured into ice water, acidified with HCl (2N), stirred for 45 min, then extracted with EtOAc. The organic extracts were dried over MgSO$_4$. Evaporation and purification by flash chromatography on silica gel (hexane/EtOAc 3/1), gave a light yellow solid (17.68 g, 82% yield, mp 145°–146° C.).

Analysis for: C$_{22}$H$_{18}$F$_3$NO$_3$ Calc'd: C, 65.83; H, 4.52; N, 3.49 Found: C, 65.78; H, 4.53; N, 3.45

Step f)
(E)-N-tert-Butoxycarbonyloxy-3-{3-[5-methyl-2-(4-trifluoromethyl-phenyl)-oxazol-4-ylmethoxy]-phenyl}-but-2-enyl)-carbamic acid tert-butyl ester In to a –20° C. solution of 3-{3-[5-methyl-2-(4-trifluoromethyl-phenyl)-oxazol-4-ylmethoxy]-phenyl}-but-2-en-1-ol (3.1 g, 7.69 mmol) in THF (50 ml), was added triphenylphosphine (2.42 g, 9.23 mmol) and tert-butyl N-(tert-butoxy-carbonyloxy) carbamate (2.15 g, 9.23 mmol). Diethylazodicarboxylate (1.45 ml, 9.23 mmol) in THF (10 ml) was then added via syringe, and the reaction was stirred for 1 h at 0° C. The reaction was poured into water, and extracted with EtOAc. The organic extracts were dried over MgSO$_4$. Evaporation and purification by flash chromatography on silica gel (hexane/EtOAc 6/1) gave a light yellow oil (4.69 g, 98% yield).

Analysis for: C$_{32}$H$_{37}$F$_3$N$_2$O$_7$ Calc'd: C, 62.13; H, 6.03; N, 4.53 Found: C, 62.17; H, 6.12; N, 4.67

Step g)
(E)-N-(3-{3-[5-methyl-2-(4-trifluoromethyl-phenyl)-oxazol-4-ylmethoxy]phenyl}-but-2-enyl)-hydroxylamine Trifluoroacetic acid (20 ml) was added in to a solution of (E)-N-tert-butoxycarbonyloxy-3-3-{3-[5-methyl-2-(4-trifluoromethyl-phenyl)-oxazol-4-ylmethoxy]-phenyl}-but-2-enyl)-carbamic acid tert-butyl ester (4.5 g, 7.28 mmol) and CH$_2$Cl$_2$ (40 ml). The reaction mixture was stirred at room temperature for 8 h. The volatiles were removed in vacuo, and the residue taken in ether/water. It was basified to pH=9–10 with NaOH (2N), and the organic layer separated and washed with water and brine. The organic layer was dried over MgSO$_4$. Evaporation and purification by flash chromatography on silica gel (hexane/EtOAc 1/1 and MeOH/EtOAc 1/10), gave a clear oil (2.70 g, 88% yield).

Analysis for: C$_{22}$H$_{21}$F$_3$N$_2$O$_3$ Calc'd: C, 63.15; H, 5.06; N, 6.70 Found: C, 63.34; H, 4.79; N, 6.53

Step h)
(E)-2-(3-{3-[5-methyl-2-(4-trifluoromethyl-phenyl)-oxazol-4-ylmethyl]-phenyl}-but-2-enyl)-[1,2,4]oxadiazolidine-3,5-dione N-(Chlorocarbonyl)isocyanate (0.548 ml, 6.22 mmol) was added dropwise to a –5° C. mixture of N-(3-{3-[5-methyl-2-(4-trifluoromethyl-phenyl)-oxazol-4-ylmethoxy]-phenyl}-but-2-enyl)-hydrozylamine (2.6 g, 6.22 mmol) in THF (25 ml). The mixture was stirred for 30 min, then poured into HCl (1N) and extracted with EtOAc. The organic extracts were dried over MgSO$_4$. Evaporation and purification by flash chromatography on acid washed (5% H$_3$PO$_4$/MeOH) silica gel (hexane/EtOAc 3/1), gave a white solid (1.85 g, 61% yield, mp 136°–138° C.).

Analysis for: C$_{24}$H$_{20}$F$_3$N$_3$O$_5$ Calc'd: C, 59.14; H, 4.13; N, 8.62 Found: C, 58.95; H, 3.92; N, 8.77

EXAMPLE 4

(E)-2-(3-{3-[5-methyl-2-(4-trifluoromethoxy-phenyl)-oxazol-4-ylmethoxy]-phenyl}-but-2-enyl)-[1,2,4]oxadiazolidine-3,5-dione The title compound was prepared in substantially the same manner as described in Example 3, and was obtained as a white solid, mp 145°–146° C.

Analysis for: $C_{24}H_{20}F_3N_3O_6$ Calc'd: C, 57.26; H, 4.00; N, 8.35 Found: C, 57.26; H, 3.94; N, 8.22

EXAMPLE 5

(E)-2-[3-(3-{5-methyl-2-[4-(2,2,2-trifluoro-ethoxy)-phenyl]-oxazol-4-ylmethoxy}-phenyl)-but-2-enyl]-[1,2,4]oxadiazolidine-3,5-dione The title compound was prepared in substantially the same manner as described in Example 3, and was obtained as a white solid, mp 145°–146° C.

Analysis for: $C_{25}H_{22}F_3N_3O_6$ Calc'd: C, 58.03; H, 4.29; N, 8.12 Found: C, 58.05; H, 3.28; N, 8.30

EXAMPLE 6

(E)-2-{3-[3-(5-methyl-2-phenyl-oxazol-4-ylmethoxy)-phenyl]-but-2-enyl}-[1,2,4]oxadiazolidine-3,5-dione The title compound was prepared in substantially the same manner as described in Example 3, and was obtained as a white solid, mp 131°–132° C.

Analysis for: $C_{23}H_{21}N_3O_5$ Calc'd: C, 65.86; H, 5.05; N, 10.02 Found: C, 65.89; H, 5.10; N, 9.87

EXAMPLE 7

(Z)-2-{3-[3-(5-methyl-2-phenyl-oxazol-4-ylmethoxy]-phenyl]-but-2-enyl}-[1,2,4]oxadiazolidine-3,5-dione The title compound was prepared in substantially the same manner as described in Example 3, and was obtained as a white solid, mp 118°–119° C.

Analysis for: $C_{23}H_{21}N_3O_5$ Calc'd: C, 65.86; H, 5.05; N, 10.02 Found: C, 65.83; H, 5.18; N, 9.97

EXAMPLE 8

(E)-2-(3-{3-[2-(5-methyl-2-phenyl-oxazol-4-yl)-ethoxy]-phenyl}-but-2-enyl)-[1,2,4]oxadiazolidine-3,5-dione The title compound was prepared in substantially the same manner as described in Example 2. The required 1-{4-[2-(5-methyl-2-phenyl-oxazol-4-yl)-ethoxy]-phenyl}-ethanone was prepared according to the following procedure. The title compound was obtained as a white solid, m.p. 142°–143° C.

Analysis for: $C_{24}H_{23}N_3O_5$ Calc'd: C, 66.50; H, 5.35; N, 9.69 Found: C, 66.18; H, 5.41; N, 9.48

Preparation of 1-{4-[2-(5-methyl-2-phenyl-oxazol-4-yl)-ethoxy]-phenyl}-ethanone

Diethylazodicarboxylate (20.7 mL, 131.6 mmol) in THF (35 mL) was added dropwise in to a cold (0° C.) solution of 4-(2'-hydroxy-ethyl)-5-methyl-2-phenyloxazole (25.0 g, 123.0 mmol), triphenylphosphine (34.5 g, 131.6 mmol), and 3'-hydroxyacetophenone (18.0 g, 131.6 mmol) and THF (180 mL). The mixture was allowed to come to room temperature and stirred for 48 hours. Then, it was poured into $H_2O$, acidified with HCl (2N) and extracted with EtOAc. The organic extracts were dried over $MgSO_4$. Evaporation and purification by flash chromatography on silica gel (hexane/EtOAc 5/1) gave a white solid (30.5 g, 77% yield, m.p. 70°–71° C.).

Analysis for: $C_{20}H_{19}NO_3$ Calc'd: C, 74.75; H, 5.96; N, 4.36 Found: C, 74.70; H, 6.15; N, 4.28

EXAMPLE 9

(E)-2-}3-[2-(5-methyl-2-phenyl-oxazol-4-ylmethyl]-benzofuran-5-yl]-but-2-enyl}-[1,2,4]oxadiazolidine-3,5-dione

Step a)
1-[2-(5-methyl-2-phenyl-oxazol-4-ylmethyl)-benzofuran-5-yl]-ethanol

Methyl magnesium chloride (4.2 ml, 12.62 mmol) was added in to a cold (0° C.) solution of 2-(5-methyl-2-phenyl-oxazol-4-ylmethyl)-benzofuran-5-carbaldehyde (prepared according to EP 0 428 312 A2, 4.0 g, 12.62 mmol) and THF (20 ml). The reaction was stirred at 0° C. for 20 min, and at room temperature for 30 min, then poured into water, acidified with HCl (2N) and extracted with EtOAc. The organic extracts were dried over $MgSO_4$. Evaporation and purification by flash chromatography on silica gel (hexane/EtOAc 2/1) gave a yellow solid (3.75 g, 88% yield, mp 103°–105° C.).

Analysis for: $C_{21}H_{19}NO_3$ Calc'd: C, 75.66; H, 5.74; N, 4.20 Found: C, 75.35; H, 5.80; N, 4.11

Step b)
1-[2-(5-methyl-2-phenyl-oxazol-4-ylmethyl)-benzofuran-5yl]-ethanone

Freshly prepared Jones' Reagent (6.5 mL, 10.51 mmol) was added dropwise in to a cold (10° C.) solution of 1-[2-(5-methyl-2-phenyl-oxazol-4-ylmethyl)-benzofuran-5-yl]-ethanol (3.5 g, 10.51 mmol) and acetone (50 mL). After 30 min, the mixture was poured into water, and extracted with ethyl ether/EtOAc:1/1. The organic extracts were dried over $MgSO_4$. Evaporation and purification by flash chromatography on silica gel (hexane/EtOAc 2/1), gave a yellow solid (3.4 g, 97% yield, mp 108°–109° C.).

Analysis for: $C_{21}H_{17}NO_3$ Calc'd: C, 76.12; H, 5.17; N, 4.23 Found: C, 76.38; H, 5.13; N, 4.09

Step c)
(E)-3-[2-(5-methyl-2-phenyl-oxazol-4-ylmethyl)-benzofuran-5-yl]-but-2-enoic acid ethyl ester The title compound was prepared in substantially the same manner as described in Example 3, step d, and was obtained as a white solid, m.p. 81°–83° C.

Analysis for: $C_{25}H_{23}NO_4$ Calc'd: C, 74.80; H, 5.77; N, 3.49 Found: C, 74.68; H, 5.75; N, 3.40

Step d)
(E)-3-[2-(5-methyl-2-phenyl-oxazol-4-ylmethyl)-benzofuran-5-yl]-but-2-en-1-ol The title compound was prepared in substantially the same manner as described in Example 3, step e, and was obtained as a white solid, m.p. 119°–121° C.

Analysis for: $C_{23}H_{21}NO_3$ Calc'd: C, 76.86; H, 5.89; N, 3.90 Found: C, 76.71; H, 5.87; N, 3.77

Step e)
(E)-1-hydroxy-1-(3-[2-(5-methyl-2-phenyl-oxazol-4-ylmethyl)-benzofuran-5-yl]-but-2-enyl)-urea Diethylazodicarboxylate (2.56 mL, 16.3 mmol) was added dropwise in to a cold (–20° C.) mixture of (E)-3-[2-(5-methyl-2-phenyl-oxazol-4-ylmethyl)-benzofuran-5-yl]-but-2-en-1-ol (4.5 g, 12.5 mmol), triphenylphosphine (4.27 g, 16.3 mmol), N,O-bis(carbophenoxy)hydroxylamine (4.45 g, 16.3 mmol) and THF (100 mL). After stirring for 30 minutes at –20° C., the mixture was allowed to come to 0° C. and stirred for 2 hours. Then, it was poured into $H_2O$ and extracted with EtOAc. The organic extracts were dried over $MgSO_4$. Evaporation gave a yellow oil (6.5), which was placed in a pressure vessel. Anhydrous ammonia (20 mL) was condensed in the vessel. The mixture was stirred at –5° C. to –10° C. for 3 hours and then at room temperature 18 hours. The excess ammonia was allowed to escape in to an acidic solution and the residue was recrystallized from ethyl ether/acetone, to give a white solid (2.5 g, 48% yield, m.p. 111°–113° C.).

Analysis for: $C_{24}H_{23}N_3O_4$ Calc'd: C, 69.05; H, 5.55; N, 10.07 Found: C, 68.66; H, 5.36; N, 9.83

Step f)
(E)-1-Methoxycarbonyloxy-1-(3-[2-(5-methyl-2-phenyl-oxazol-4-ylmethyl)-benzofuran-5-yl]-but-2-enyl)-urea Sodium hydride (0.3 g, 10.0 mmol) was added portionwise in to a cold (0°) solution of (E)-1-hydroxy-1-(3-[2-(5-methyl-2-phenyl-oxazol-4-ylmethyl)-benzofuran-5-yl]-but-2-enyl)-urea (1.9 g, 4.55 mmol) and THF (20 mL). After stirring for 1 hour, methyl chloroformate (1.6 mL, 18.2 mmol) was added dropwise. The reaction mixture was stirred for 1 hour, poured in to dioxane (50 mL)/MaOH (2N, 5 mL) solution and after 10 minutes acidified with HCl (2N) and extracted with EtOAc. The organic extracts were dried over $mgSO_4$. Evaporation and purification by flash chromatography on silicagel (hexane/EtOAc 2/1), gave a yellow solid (1.72 g, 79% yield, m.p. 65°–67° C.).

Analysis for: $C_{26}H_{25}N_3O_6$ Calc'd: C, 65.68; H, 5.30; N, 8.84 Found: C, 65.94; H, 5.06; N, 8.83

Step g)
(E)-2-{3-[2-(5-methyl-2-phenyl-oxazol-4-ylmethyl)-benzofuran-5-yl]-but-2-enyl}-[1,2,4]oxadiazolidine-3,5-dione Sodium hydride (76 mg, 2.52 mmol) was added portionwise in to a cold (0°) solution of E)-N-carbomoyl-N-methoxycarbonyloxy-3-[2-(5-methyl-2-phenyl-oxazol-4-ylmethyl)-benzofuran-5-yl]-but-2-enyl-amine (1.2 g, 2.52 mmol) and DMF (10 mL). The reaction mixture was stirred for 30 minutes and then poured into water (10 mL), acidified with HCl (2N) and extrated with EtOAc. The organic extracts were dried over $MgSO_4$. Evaporation and crystallization from ethyl ether, gave a yellow solid (0.72 g, 65% yield, m.p. 163–165).

Analysis for: $C_{25}H_{21}N_3O_5$ Calc'd: C, 67.71; H, 4.77; N, 9.47 Found: C, 67.79; H, 4,56; N, 9.39

EXAMPLE 10

(E)-2-(2-methyl-3-{4-[5-methyl-2-(4-trifluoromethyl-phenyl)-oxazol-4-ylmethoxy]-phenyl}-allyl)-[1,2,4]oxadiazolidine-3,5-dione

Step a)
(E)-2-methyl-3-{3-[5-methyl-2-(4-trifluoromethyl-phenyl)-oxazol-4-ylmethoxy]-phenyl}-acrylic acid ethyl ester Triethyl 2-phosphonopropionate (2.64 ml, 11.08 mmol) was added dropwise in to a cold (0° C.) suspension of sodium hydride (0.31 g, 10.52 mmol) and toluene (50 ml). After the addition, the mixture was stirred for 1 hour, and then 3-[5-methyl-2-(-4-trifluoromethyl-phenyl)-oxazol-4-ylmethoxy)-benzaldehyde (2.0 g, 5.54 mmol) in THF (10 ml) was added dropwise. The reaction mixture was stirred at room temperature for 24 hours, poured into water, acidified with HCl (2N), and extracted with EtOAc. The organic extracts were dried over $MgSO_4$. Evaporation and purification by flash chromatography on gel (hexane/EtOAc 8/1) gave a clear oil (2.2 g, 89% yield).

Analysis for: $C_{24}H_{22}F_3NO_4$ Calc'd: C, 64.82; H, 4.99; N, 2.93

Step b)
(E)-2-methyl-3-{3-[5-methyl-2-(4-trifluoromethyl-phenyl)-oxazol-4ylmethoxy]-phenyl}-prop-2-en-1-ol The title compound was prepared in substantially the same manner as described in Example 3, step e, and was obtained as a white solid, m.p. 90°–91° C.

Analysis for: $C_{22}H_{20}F_3NO_3$ Calc'd: C, 65.50; H, 4.99; N, 3.47 Found: C, 65.40; H, 5.12; N, 3.33

Step c)
(E)-2-methyl-3-{3[5-methyl-2-(4-trifluoromethyl-phenyl)-oxazol-4-ylmethyoxy]-allyl)-hydroxylamine The title compound was prepared in substantially the same manner as described in Example 2, step b, and was obtained as a yellow oil.

Analysis for: $C_{22}H_{21}F_3N_2O_3$ Calc'd: C, 63.15; H, 5.06; N,6.69 Found: C, 62.82; H, 4.99; N,6.64

Step d)
(E)-2-(2-methyl-3-{4-[5-methyl-2-(4-trifluoromethyl-phenyl)-oxazol-4-ylmethoxy]-phenyl}-allyl)-[1,2,4]oxadiazolidine-3,5-dione The title compound was prepared in substantially the same manner as described in Example 1, step h, and was obtained as a white solid, mp 144°–146° C.

Analysis for: $C_{24}H_{20}F_3O_5$ Calc'd: C, 59.14; H, 4.13; N, 8.62 Found: C, 59.20; H, 3.95; N, 8.57

EXAMPLE 11

(E)-2-(2-ethyl-3-{3-[5-methyl-2-(4-trifluoromethyl-phenyl)-oxazol-4-ylmethoxy]-phenyl}-allyl-[1,2,4]oxadiazolidine-3,5-dione The title compound was prepared in substantially the same manner as described in Example 10, and was obtained as a white solid, mp 124°–125° C.

Analysis for: $C_{25}H_{22}F_3N_3O_5$ Calc's: C, 59.88; H, 4.42; N, 8.38 Found: C, 59.94; H, 4.40; N, 8.34

EXAMPLE 12

2-(1-Methyl-3-{3-[5-methyl-2-(4-trifluoromethyl-phenyl)-oxazol-4-ylmethoxy]-phenyl}-allyl)-[1,2,4]oxadiazolidine-3,5-dione

Step a)
3-[5-Methyl-2-(4-trifluoromethyl-phenyl)-oxazol-4-ylmethoxy]-benzaldehyde The title compound was prepared in substantially the same manner as described in example 1, step a and was obtained as a yellow solid, mp104°–105° C.

Analysis for: $C_{19}H_{14}F_3NO_3$ Calc'd: C, 63.16; H, 3.91; N, 3.88 Found: C, 62.84; H, 3.97; N, 3.87

Step b)
(E)-4-{3-[5-Methyl-2-(4-trifluoromethyl-phenyl)-oxazol-4-ylmethoxyl-phenyl}-but-3-en-2-one A solution of sodium hydroxide (1.13 g, 28.25 mmol) in water (15 mL), was added to a mixture of 3-[5-methyl-2-(4-trifluoromethyl-phenyl)-oxazol-4-ylmethoxy]-benzaldehyde (6.0 g, 16.62 mmol) and acetone (100 mL). The reaction was stirred for 1 hour, and the excess acetone was removed in vacuo. The residue was acidified with HCl (1N), stirred for 10 min, then extracted with EtOAc. The organic extracts were dried over $MgSO_4$. Evaporation and purification by flash chromatography on silica gel (EtOAc4/1) gave a white solid (4.6 g, 69% yield, mp 84°–84° C.).

Analysis for: $C_{22}H_{18}F_3NO_3$ Calc'd: C, 65.83; H, 4.52; N, 3.49 Found: C, 65.74; H, 4.41; N, 3.52

Step c)
(E)-4-{5-Methyl-2-(4-trifluoromethyl-phenyl)-oxazol-4-ylmethoxy]-phenyl}-but-3-en-2-ol Sodium borohydride (0.389 g, 10.22 mmol) was added to a −20° C. solution of (E)-4-{3-[5-methyl-2-4trifluoromethyl-phenyl)-oxazol-4-ylmethoxy]-phenyl}-but-3-en-2-one (4.1 g, 10.22 mmol), cerium trichloride (3.81 g, 10.22mmol), methanol (150 mL), and THF (30 mL). The reaction was stirred for 30 min, then poured into water, acidified with HCl (2N), an extracted with EtOAc. The organic extracts were dried over $MgSO_4$. Evaporation and purification by flash chromatography on silica gel (hexane/EtOAc 2/1), gave a white solid (3.7 g, 89% yield, m.p. 48–50° C.).

Analysis for: $C_{22}H_{20}F_3NO_3$ Calc'd: C, 65.50; H, 4.99; N, 3.47 Found: C, 65.78; H, 5.07; N, 3.58

Step d)
(E)-N-(1-Methyl-3-{3-[5-methyl-2-(4-trifluoromethyl-phenyl)-oxazol-4-ylmethoxyl-phenyl}-allyl)-hydroxylamine The title compound was prepared in substantially the same manner as described in Example 1, step b, and was obtained as a white solid, m.p. 118°–120° C.

Analysis for: $C_{22}H_{21}F_3N_2O_3$ Calc'd: C, 63.15; H, 5.06; N, 6.69 Found: C, 62.72; H, 5.04; N, 6.59

Step e)
2-(1-methyl-3-{3-[5-methyl-2-(4-trifluoromethyl-phenyl)-oxazol-4-ylmethoxy]-phenyl}-ally)-[1,2,4]oxadiazolidine-3,5-dione The title compound was prepared in substantially the same manner as described in Example 2, step c, and was obtained as a white solid, m.p. 119°–121° C.

Analysis for: $C_{24}H_{20}F_3N_3O_5$ Calc'd: C, 59.14; H, 4.13; N, 8.62 Found: C, 59.00; H, 3.96; N, 8.82

EXAMPLE 13

(E)-2-(3-{3-[2-(4-chloro-phenyl)-5-methyl-oxazol-4-ylmethoxy]-phenyl}-1-methyl-ally)-[1,2,4]oxadiazolidine-3,5-dione The title compound was prepared in substantially the same manner as described in Example 12, and was obtained as a white solid, m.p. 172°– C.

Analysis for: $C_{23}H_{20}ClN_3O_5$ Calc'd: C, 60.86; H, 4.44; N, 9.26 Found: C, 60.92; H, 4.39; N, 9.17

EXAMPLE 14

(E)-2-(2-methyl-3-{3-[5-methyl-2-(4-trifluoromethyl-phenyl)-oxazol-4-ylmethoxy]-phenyl}-but-2-enyl)-[1,2,4 oxadiazolidine-3,5-dione Step a) (E)-2-methyl-3-{3-[5-methyl-2-(4-trifluoromethyl-phenyl)-oxazol-4-ylmethoxyl-phenyl}-but-2-enoic acid ethyl ester, (Z)-2-methyl-3-{3-[5-methyl-2-(4-trifluoromethyl-phenyl)-oxazol-4-ylmethoxyl-phenyl}-but-2-enoic acid ethyl ester The title compounds was prepared in substantially the same manner as described in Example 1, step c, and were obtained as white solids.

(trans-)
Analysis for: $C_{25}H_{24}F_3NO_4$ Calc'd: C, 65.35; H, 5.26; N, 2.3.05 Found: C, 66.74; H, 5.39N, 2.84

(cis-)
Analysis for: $C_{25}H_{24}F_3NO_4$ Calc'd: C, 65.45; H, 5.26; N, 3.05 Found: C, 65.45; H, 5.29; N, 2.80

Step b) (E)-2-methyl-3-{3-[5-methyl- 2-(4-trifluoromethyl-phenyl)-oxazol-4-ylmethoxyl]-phenyl}-but-2-en-1-ol The title compound was prepared in substantially the same manner as described in Example 2, step a, and was obtained as a white solid, m.p. 115°–116° C.

Analysis for: $C_{23}H_{22}F_3NO_3$ Calc'd: C, 66.18; H, 5.31; N, 3.56 Found: C, 66.04; H, 5.32; N, 3.49

Step c) (E)-N-(2-Methyl-3-{3-[5-methyl-2-(4trifluoromethyl-phenyl)-oxazol-4-ylmethoxyl-phenyl}-but-2-enyl)-hydroxylamine The title compound was prepared in substantially the same manner as described in Example 2, step b, and was obtained as a white solid, m.p. 115°–116° C.

Analysis for: $C_{23}F_{23}N_2O_3 \times 1H_2O$ Calc'd: C, 61.33; H, 5.55; N, 6.22 Found: C, 61.34; H, 5.57; N, 5.84

Step d) (E)-2-2-methyl-2-(4-trifluoromethyl -phenyl))-oxazol-4-ylmethoxyl-phenyl}-but-2-enyl) -[1,2,4]oxadiazolidine -3.5-dione The title compound was prepared in substantially the same manner as described Example 2, step c, and was obtained as a white solid, m.p. 152°–153° C.

EXAMPLE 15

(Z)-2-(2-methyl-3-{3-[5-methyl-2-(4-trifluoromethyl-phenyl)-oxazol-4-ylmethoxy]-phenyl}1,2,4] oxadiazolidine-3,5-dione The title compound was prepared in substantially the same manner as described in Example 13, and was obtained as a white solid, m.p. 114°–145° C.

Analysis for: $C_{25}H_{22}F_3N_3O_5$ Calc'd: C, 59.88; H, 4.42; N, 8.38 Found: C, 59.69; H, 4.45; N, 8.37

EXAMPLE 16

(E)-2-(1-methyl-3-{3-[5-methyl-2-(4-trifluoromethyl-phenyl)-oxazol-4-ylmethoxy]-phenyl}-but-2-enyl}-[1,2,4]oxadiazolidine-3,5-dione

Step a)
(E)-3-{3-[5-Methyl-2-(4-trifluoromethyl-phenyl)-oxazol-4-ylmethoxyl]-phenyl}-but-2-enal In to a solution of (E)-3-{3-[5-methyl-2-(4-trifluoromethyl-phenyl)-oxazol-4-ylmethoxy]-phenyl}-but-2-en-1-ol (21.48 g, 53.3 mmol) in $CH_2Cl_2$(500 ml), was added manganese dioxide (27.8 g, 319.8 mmol), and the reaction was stirred at room temperature for 60 h. The mixture was filtered through solka floc. Evaporation and purification by flash chromatography on silica gel (hexane/EtOAc 7/1), gave a light yellow solid (17.68 g, 82% yield, m.p. 145°–146° C.).

Analysis for: $C_{22}H_{18}F_3NO_3$ Calc'd: C, 65.83; H, 4.52; N, 3.49 Found: C, 65.78; H, 4.53; N, 3.45

Step b)
(E)-4-{3-[5-Methyl-2-(4-trifluoromethyl-phenyl)-oxazol-4-ylmethoxy]-phenyl}-pent-3-en-2-ol Methyl magnesium bromide (3.0M in ether) (13.9 ml, 41.4 mmol) was added to a 0° C. mixture of (E)-3-{3-[5-methyl-2-(4-trifluoromethyl-phenyl)-oxazol-4-ylmethoxy]-phenyl}-but-2-enal(16.68 g, 41.6 mmol) in THF (200 ml). The reaction was stirred at 0°–5° C. for 25 min, then poured into water, acidified with HCl (2N), and extracted with EtOAc. The organic extracts were dried over $MgSO_4$. Evaporation and purification by flash chromatography on silica gel (hexane/EtOAc 4/1), gave a yellow solid (5.85 g, 33% yield, m.p. 45°–47° C.).

Analysis for: $C_{23}H_{22}F_3NO_3$ Calc'd: C, 66.18; H, 5.31; N, 3.36 Found: C, 65.97; H, 5.24; N, 3.34

Step c)
(E)-N-(1-Methyl-3-{3-[5-methyl-2-(4-trifluoromethyl-phenyl)-oxazol-4-ylmethoxy]-phenyl}-but-2-enyl)-hydroxylamine The title compound was prepared in substantially the same manner as described in Example 2, step b, and was obtained as a clear oil.

Analysis for: $C_{23}H_{23}F_3N_2O_3$ Calc'd: C, 63.88; H, 5.36; N, 6.48 Found: C, 63.48; H, 5.33; N, 5.08

Step d)
(E)-2-(1-methyl-3-{3-[5-methyl-2-(4-trifluoromethyl-phenyl)-oxazol-4-ylmethoxy]-phenyl}-but-2-enyl}-[1,2,4]oxadiazolidine-3,5-dione The title compound was prepared in substantially the same manner as described in Example 2, step c, and was obtained as a white solid (0.31 g, 27% yield, mp 55°–56° C.).

Analysis for: $C_{25}H_{22}F_3N_3O_5$ Calc'd: C, 59.88; H, 4.42; N, 8.38 Found: C, 60.14; H, 4.49; N 8.32

EXAMPLE 17

(E)-2-(3-{4-[5-Methyl-2-(4-trifluoromethyl-phenyl)-oxazol-4-ylmethoxy]-phenyl}-allyl)-[1,2,4] oxadiazolidine-3,5-dione

Step a)
(E)-3-{3-[5-methyl-2-(4-trifluoromethyl-phenyl)-oxazol-4-ylmethoxy]-phenyl}-acrylic ethyl ester Triethylphosphonoacetate (4.38 ml, 22.06 mmol) was added dropwise in to a cold (0° C.) suspension of sodium hydride (0.59 g, 19.74 mmol) and toluene (100 mL). After the addition, the mixture was stirred for 1 hour, and then 3-[5-methyl-2-(-4-trifluoromethyl-phenyl)-oxazol-4-ylmethoxy)-benzaldehyde (5.7 g, 15.79 mmol) in THF (20 ml) was added dropwise. The reaction mixture was stirred at room temperature for 1 hour, poured into water, acidified with HCl (2N), and extracted with EtOAc. The organic extracts were dried over $MgSO_4$. Evaporation and purification by flash chromatography on silica gel (hexane/EtOAc 5/1), gave a white solid (6.3 g, 93% yield, m.p. 79°–80° C.).

Analysis for: $C_{23}H_{18}F_3N_3O_5$ Calc'd: C, 64.03; H, 4.67; N, 3.25 Found: C, 64.25; H, 4.63; N, 3.16

Step b)
(E)-{3-[5-Methyl-2-(4-trifluoromethyl-phenyl)-oxazol-4-ylmethoxy]-phenyl}-prop-2-en-1-ol The title compound was prepared in substantially the same manner as described in Example 1, step d, and was obtained as a white solid, m.p. 117°–118° C.

Analysis for: $C_{21}H_{18}F_3NO_3$ Calc'd: C, 64.78; H, 4.66; N, 3.59 Found: C, 64.60; H, 4.54; N, 3.65

Step c)
(E)-N-(3-{3-[5-methyl-2-(4-trifluoromethyl-phenyl)-oxazol-4-ylmethoxy]phenyl}-allyl)-hydroxylamine The title compound was prepared in substantially the same manner as described in Example 2, step b, and was obtained as a white solid, m.p. 128°–130° C.

Analysis for: $C_{21}H_{19}F_3N_2O_3$ Calc'd: C, 62.37; H, 4.73; N, 6.93 Found: C, 62.17; H, 4.71; N, 6.79

Step d)
(E)-2-(3-{4-[5-methyl-2-(4-trifluoromethyl-phenyl)-oxazol-4-ylmethoxy]-phenyl}-allyl)-[1,2,4] oxadiazolidine-3,5-dione The title compound was prepared in substantially the same manner as described in Example 1, step g, and was obtained as a white solid, m.p. 179°–181° C.

Analysis for: $C_{23}H_{18}F_3N_3O_5$ Calc'd: C, 58.35; H, 3.83; N, 8.88 Found: C, 58.47; H, 3.70; N, 8.86

EXAMPLE 18

(E)-2-(2-{3-[5-methyl-2-(4-trifluoromethyl-phenyl)-oxazol-4-ylmethoxy]]-phenyl}-cyclopropylmethyl)-[1,2,4]oxadiazolidine-3,5-dione (E)-2-(2-{5-methyl-2-(4-trifluoromethyl-phenyl)-oxazol-4-ylmethoxy]-phenyl}-cyclopropylmethyl)-[1,2,4]oxadiazolidine-3,5-dione Step a) (E)-2-{3-[5-Methyl-2-(4-trifluoromethyl-phenyl)-oxazol-4-ylmethoxy]-phenyl}-cyclopropyl)-methanol Chloroiodomethane (3.37 mL, 46.28 mmol) was added dropwise in a cold (0° C.) solution of diethyzinc (23.14 mL, 23.14 mmol) and dichloroethane (40 mL). After stirring for 10 minutes (E)-{3-[5-methyl-2-(4-trifluoromethyl-phenyl)-oxazol-4-ylmethoxy]-phenyl}-prop-2-en-1-ol (4.5 g, 11.57 mmol) in dichloromethane (10 mL) was added dropwise. The reaction mixture was stirred for 1 hour, quenched with aqueous NH$_4$Cl and allowed to come to room temperature. After 15 minutes it was poured into water and extracted with ethyl ether. The organic extracts were dried over MgSO$_4$. Evaporation and purification by flash chromatography on silica gel (hexane /EtOAc 3/2), gave a clear oil (2.8 g, 80% yield).

Analysis for: $C_{22}H_{20}F_3NO_3$ Calc'd: C, 65.50; H, 5.00; N, 3.47 Found: C, 65.36; H, 5.12; N, 3.43

Step b) (E)-N-(2-{3-[5-methyl-2-(trifluoromethyl-phenyl)-oxazol-4-ylmethoxy]-phenyl}-cyclopropylmethyl)-hydroxylamine The title compound was prepared in substantially the same manner as described in Example 2, step b, and was obtained as a clear oil.

Analysis for: $C_{22}H_{21}F_3N_2O_3$ Calc'd: C, 63.15; H, 5.06; N, 6.69 Found: C, 62.90; H, 5.07; N, 6.66

Step c) (E)-2-(2-{3-[5-methyl-2-(4-trifluoromethyl-phenyl)-oxazol-4-ylmethoxy]-phenyl}-cyclopropylmethyl)-[1,2,4}oxadiazolidine-3,5-dione The title compound was prepared in substantially the same manner as described in Example 1, step g, and was obtained as a white solid, m.p.126°–128° C.

Analysis for: $C_{24}H_{20}F_3N_3O_5$ Calc'd: C, 59.14; H, 4.14; N, 8.62 Found: C, 59.27; H, 3.99; N, 8.78

EXAMPLE 19

(E)-2-(2-methyl-2-{3-[5-methyl-2-(4-trifluoromethoxy-phenyl)-oxazol-4-ylmethoxy]-phenyl}-cyclopropylmethyl)-[1,2,4}oxadiazolidine-3,5-dione The title compound was prepared in substantially the same manner as described in Example 17, and was obtained as a white solid, m.p. 42°–43° C.

Analysis for: $C_{25}H_{22}F_3N_3O_6$ Calc'd: C, 58.03; H, 4.28; N, 8.12 Found: C, 57.69; H, 4.32; N, 8.09

EXAMPLE 20

(E, E)-2-{5-[3-(5-methyl-2-phenyl-oxazol-4-ylmethoxy)-phenyl]-hexa-2,4-dienyl}-[1,2,4]oxadiazolidine-3,5-dione Step a) (E, E)-5-[3-(5-Methyl-2-phenyl-oxazol-4-ylmethoxy]-phenyl)-hexa-2,4-dienoic acid ethyl ester Lithium bis(trimethylsilyl)amide (45.12 mL, 45.12 mmol) was added dropwise in to a cold solution fo triethyl 4-phosphonocrotonate (10.0 ml, 45.12 mmol) in THF (200 mL). After stiring for 1 hour, 1-(3-[5-methyl-2-phenyl-oxazol-4-ylmethoxy]-phenyl)-ethanone (12.0 g, 39.1 mmol) in THF (50 mL) was added dropwise. The reaction mixture was allowed to come to room temperature and stirred for 24 hours. Then, it was quenched with aqueous NH4Cl, poured into water, acidified with HCL (2N), and extracted with EtOAc. The organic extracts were dried over MgSO$_4$. Evaporation and purification by flash chromatography on silica gel (hexane/EtOAc 8/1), gave a yellow oil (9.6 g, inseparable mixture of cis- and trans- isomers).

Analysis for: $C_{25}H_{25}NO_4 \times 0.25\ H_2O$ Calc'd: C, 73.62; H, 6.26; N, 3.43 Found: C, 73.69; H, 5.86; N, 3.44

Step b) (E, E)-5-[3-(5-Methyl-2-phenyl-oxazol-4-ylmethoxy]-phenyl)-hexa-2,4-dien-1-ol Di-isobutyl aluminum hydride (1.0M in THF, 55.83 ml, 55.83 mmol) was added dropwise in to a cold (–50° C.) solution of (E, E)-5-(3-[5-methyl-2-phenyl-oxazol-4-yl-methoxy]-phenyl)-hexa-2,4-dienoic acid ethyl ester(7.5 g, 18.61 mmol, mixture of cis- and transisomers), THF (100 ml) and ethyl ether (100 mL). The reaction was warmed to 0° C. and stirred for 1 hour. The reaction mixture was quenched with acetone (dropwise addition), methanol, poured into water, acidified with HCl (2N), and extracted with EtOAc. The organic extracts were dried over MgSo$_4$. Evaporation and purification by flash chromatography on silica gel (hexane/EtOAc 4/1), gave the trans- (4.9 g), and the cis-(1.7 g) isomers as yellow oils.

(trans-)

Analysis for: $C_{23}H_{23}NO_3$ Calc'd: C, 76.43; H, 6.41; N, 3.88 Found: C, 76.25; H, 6.36; N, 4.03

(cis-)

Analysis for: $C_{23}H_{23}NO_3$ Calc'd: C, 76.43; H, 6.41; N, 3.88 Found: C, 75.98; H, 6.21; N, 3.69

Step c) (E, E)-N-(5-[3-(5-Methyl-2-phenyl-oxazol-4-ylmethoxy]-phenyl)-hexa-2,4-dienyl)-hydroxylamine The title compound was prepared in substantially the same manner as described in Example 2, step b, and was obtained as a light yellow oil.

Analysis for: $C_{23}H_{24}N_2O_3$ Calc'd: C, 73.38; H, 6.43; N, 7.44 Found: C, 73.41; H, 6.45; N, 7.20

Step d) (E, E)-2-{5-[3-(5-methyl-2-phenyl-oxazol-4-ylmethoxy)-phenyl]-hexa-2,4-dienyl}-[1,2,4]oxadiazolidine-3,5-dione The title compound was prepared in substantially the same manner as described in Example 2, step c, and was obtained as a white solid, m.p. 151°–152° C.

Analysis for: $C_{25}H_{23}N_3O_5$ Calc'd: C,67.40; H, 5.20; N, 9.43 Found: C, 67.70; H, 5.28; N, 9.35

EXAMPLE 21

(Z, E)-2-{5-[3-(5-methyl-2-phenyl-oxazol-4-ylmethoxy)-phenyl]-hexa-2,4-dienyl}-[1,2,4]oxadiazolidine-3,5-dione The title compound was prepared in substantially the same manner as described in Example 20, and was obtained as a white solid, m.p. 117°–118° C.

Analysis for: C$_{25}$H$_{23}$N$_3$O$_5$ Calc'd: C, 67.40; H, 5.20; N, 9.43 Found: C, 67.32; H, 5.21; N, 9.32

EXAMPLE 22

2-(1-methyl-3-{3-[5-methyl-2-(4-trifluoromethyl-phenyl)-oxazol-4-ylmethoxy]-phenyl}-prop-2-ynyl)-[1,2,4]oxadiazolidine-3,5-dione Step a) 4-(3-Ethynyl-phenoxymethyl)-5-methyl-2-(4-trifluoromethyl-phenyl)-oxazole (Bromomethyl)triphenylphosphonium bromide (21.2 g, 48.61 mmol) was added portionwise to a −78° C. mixture of potassium-tert-butoxide (10.9 g, 97.23 mmol) in THF (200 mL). The mixture was stirred for 2 h, then 3-[5-methyl-2-(4-trifluoromethyl-phenyl)-oxazol-4-ylmethoxy]-benzaldehyde (11.7 g, 32.41 mmol) in THF (50 mL) was added dropwise. The mixture was stirred for 1 hour at −78° C., then at room temperature for 2 days. The reaction mixture was quenched with aqueous NH$_4$Cl, poured into water, acidified with HCl (2N), and extracted with EtOAc. The organic extracts were dried over MgSO$_4$. Evaporation and purification by flash chromatography on silica gel (hexane/EtOAc 8/1) gave a white solid (7.5 g, 67% yield, mp 62°–64° C.).

Analysis for: C$_{20}$H$_{14}$F$_3$NO$_2$×0.25 H$_2$O Calc'd: C, 66.39; H, 4.01; N, 3.87 Found: C, 66.67; H, 3.75; N, 4.15

Step b) 4-{3-[5-methyl-2-(4-trifluoromethyl-phenyl)-oxazol-4-ylmethoxy]-phenyl}-but-3-yn-2-ol Lithium bis(trimethylsilyl)amide (10.5 mL, 10.5 mmol) was added to a cold (0° C.) solution of 4-(3-ethynyl-phenoxymethyl)-5-methyl-2-(4-trifluoromethyl-phenyl)-oxazole (3.0 g, 8.77 mmol) in THF (100 mL). After 1 h at 0° C., acetaldehyde (0.59 mL, 10.5 mmol) was added dropwise. The mixture was stirred for 30 min, then quenched with aqueous NH$_4$Cl, poured into water, acidified with HCl (2N), and extracted with EtOAc. The organic extracts were dried over MgSO$_4$. Evaporation and purification by flash chromatography on silica gel(hexane/EtOAc 4/1) gave a yellow solid (2.1 g, 59% yield, m.p. 86°–87° C.).

Analysis for: C$_{22}$H$_{18}$F$_3$NO$_3$ Calc'd: C, 65.83; H, 4.52; N, 3.49 Found: C, 65.89; H, 4.38; N, 3.36 step c) N-(1-Methyl-3-{3-[5-methyl-2-(4-trifluoromethyl-phenyl)-oxazol-4-ylmethoxy]-phenyl}-prop-2-ynyl)-hydroxylamine The title compound was prepared in substantially the same manner as described in Example 2, step b, and was obtained as a light yellow solid, m.p. 110°–112° C.

Analysis for: C$_{22}$H$_{19}$F$_3$N$_2$O$_3$ Calc'd: C, 63.46; H, 4.60; N, 6.73 Found: C, 66.71; H, 4.56; N, 6.69

Step d) 2-(1-methyl-3-{3-[5-methyl-2-(4-trifluoromethyl-phenyl)-oxazol-4-ylmethoxy]-phenyl}-prop-2-ynyl)-[1,2,4]oxadiazolidine-3,5-dione The title compound was prepared in substantially the same manner as described in Example 1, step g, and was obtained as a white solid, m.p. 84°–86° C.

Analysis for: C$_{24}$H$_{18}$F$_3$N$_3$O$_5$ Calc'd: C, 59.38; H, 3.74; N, 8.66 Found: C, 59.38; H, 3.50; N, 8.56

EXAMPLE 23

2-{1-methyl-3-[3-(5-methyl-2-phenyl-oxazol-4-ylmethoxy)-phenyl]-prop-2-ynyl}-[1,2,4]oxadiazolidine-3,5-dione The title compound was prepared in substantially the same manner as described in Example 21, and was obtained as a white solid, m.p. 55°–57° C.

Analysis for: C$_{23}$H$_{19}$N$_3$O$_5$×0.25 H$_2$O Calc'd: C, 65.40; H, 4.01; N, 9.95 Found: C, 65.20; H, 4.36; N, 10.23

EXAMPLE 24

(E)-5-{3-[3-(5-methyl-2-phenyl-oxazol-4-ylmethyl]-phenyl]-but-2-enyl}-oxazolidine-2,4-dione Step a) (E)-4-[3-(3-Chloro-1-methyl-propenyl)-phenoxymethyl]-5-methyl-2-phenyl-oxazole 3-[3-(5-Methyl-2-phenyl-oxazol-4-ylmethoxy)-phenyl]-but-2-en-1-ol (10.0 g, 29.85 mmol) in ether (50 mL) was added to a cold (0° C.) suspension of phosphorus oxychloride (9.31 g, 44.77 mmol), calcium carbonate (4.47 g, 44.77 mmol), and ether (300 mL). After 30 minutes, the reaction mixture was poured into water. The organic layer was separated, washed with water and brine. The organic extracts were dried over MgSO$_4$. Evaporation and purification by flash chromatography on silica gel (hexane/EtOAc 5/1) gave a clear oil (9.1 g, 86% yield).

Analysis for: C$_{21}$H$_{20}$ClNO$_2$ Calc'd: C, 71.28; H, 5.70; N, 3.96 Found: C, 71.42; H, 5.71; N, 3.88

Step b) (E)-5-{3-[3-(5-methyl-2-phenyl-oxazol-4-ylmethyl]-phenyl]-but-2-enyl}-oxazolidine-2,4-dione Tert-butyl lithium (17.5 mL, 29.7 mmol) was added dropwise in to a rapidly stirred cold (−78° C.) solution of lithium chloride (3.6 g, 84.84 mmol) and oxazolidine-2,4-dione (1.43 g, 14.14 mmol) in THF (90 mL). The mixture was stirred at −78° C. for 30 minutes, then gradually warmed to 0° C. After recooling to −78° C., (E)-4-[3-(3-chloro-1-methyl-propenyl)-phenoxymethyl]-5-methyl-2-phenyl-oxazole (5.0 g, 14.14 mmol) in THF (5 mL) was added all at once. After stirring for 10 minutes at −78° C., the mixture was gradually warmed to room temperature, and allowed to stir for 5 hours. Then, the reaction mixture was quenched with aqueous NH$_4$Cl, poured into water, acidified with HCl, and extracted with EtOAc. The organic extracts were dried over MgSO$_4$. Evaporation and purification by flash chromatography on silica gel (hexane/EtOAc 3/1), gave a white solid (3.5 g, 59% yield, m.p. 138°–139° C.).

Analysis for: C$_{24}$H$_{22}$N$_2$O$_5$ Calc'd: C, 68.89; H, 5.30; N, 6.69 Found: C, 68.49; H, 5.29; N, 6.71

EXAMPLE 25

(E)-5-[3-(3-{5-methyl-2-[4-(2,2,2-trifluoro-ethoxy)-phenyl]-oxazol-4-ylmethoxy}-phenyl)-but-2-enyl]-oxazolidine-2,4-dione The title compound was obtained in substantially the same manner as described in Example 24, and was obtained as a white solid, m.p. 120°–121° C.

Analysis for: C$_{26}$H$_{23}$F$_3$N$_2$O$_6$ Calc'd: C, 60.46; H, 4.49; N, 5.42 Found: C, 60.62; H, 4.47; N, 5.18

EXAMPLE 26

(E)-5-(3-{3-[5-methyl-2-(4-trifluoromethoxy-phenyl)-oxazol-4-ylmethoxy]-phenyl}-but-2-enyl)-oxazolidine-2,4-dione The title compound was obtained in substantially the same manner as described in Example 24, and was obtained as a white solid, m.p. 105°–106° C.

Analysis for: $C_{25}H_{21}F_3N_2O_6$ Calc'd: C, 59.76; H, 4.21; N, 5.58 Found: C, 59.92; H, 4.12; N, 5.54

EXAMPLE 27

(E)-5-(3-{3-[2-(5-methyl-2-phenyl-oxazol-4-yl)-ethoxy]-phenyl}-but-2-enyl)-oxazolidine-2,4-dione The title compound was obtained in substantially the same manner as described in Example 24, and was obtained as a white solid, m.p. 100°–101° C.

Analysis for: $C_{25}H_{24}N_2O_5$ Calc'd: C, 69.43; H, 5.59; N, 6.48 Found: C, 69.59; H, 5.89; N, 6.16

EXAMPLE 28

(E)-5-{3-[3-(5-methyl-2-phenyl-oxazol-4-ylmethoxy)-phenyl]-but-2-enyl}-thiazolidine-2,4-dione Butyl lithium (16.6 mL, 41.58 mmol) was added dropwise in to a cold (−78° C.) solution of thiazolidine-2,4-dione (2.31 g, 19.8 mmol) and THF (80 mL). The mixture was stirred at −78° C. for 15 minutes, then gradually warmed to 0° C., and stirred for 30 minutes to complete the dianion formation. After recooling to −78° C., 4-[3-(3-chloro-1-methyl-propenyl)-phenoxymethyl]-5-methyl-2-phenyl-oxazole (7.0 g, 19.8 mmol) in THF (15 mL) was added all at once. After stirring for 30 minutes at −78° C., the mixture was gradually warmed to room temperature, and allowed to stir for 2 hours. Then, the reaction mixture was quenched with aqueous $NH_4Cl$, poured into water, acidified with HCl, and extracted with EtOAc. The organic extracts were dried over $MgSO_4$. Evaporation and purification by flash chromatography on acid washed (5% $H_3PO_4$/MeOH) silica gel (hexane/EtOAc 3/1), gave a white solid (2.9 g, 33% yield, m.p. 48°–49° C.).

Analysis for: $C_{24}H_{22}N_2O_4S \times 0.25 H_2O$ Calc'd: C, 65.68; H, 5.13; N, 6.38 Found: C, 65.72; H, 5.19; N, 6.45

EXAMPLE 29

(E)-5-(3-{3-[5-methyl-2-(4-trifluoromethoxy-phenyl)-oxazol-4-ylmethoxy]-phenyl}-but-2-enyl)-thiazolidine-2,4-dione The title compound was obtained in substantially the same manner as described in Example 27, and was obtained as a light yellow solid, m.p. 50°–51° C.

Analysis for: $C_{25}H_{21}F_3N_2O_5S$ Calc'd: C, 57.91; H, 4.08; N, 5.40 Found: C, 57.57; H, 4.16; N, 5.30

Pharmacology

Determination of Blood Glucose Lowering in db/db Mice.

On the morning of Day 1, 35 mice [male diabetic db/db (C57BL/KsJ) mice (Jackson Laboratories), 2–7 months of age and 50–70 g] were fasted for 4 hours, weighed and a baseline blood sample (15–30 μl) was collected from the tail-tip of each mouse without anesthesia, and placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, 5 mice having the most extreme (i.e., highest or lowest) plasma glucose levels were excluded and the remaining 30 mice were randomly assigned into 7 groups of equivalent mean plasma glucose levels (N=6 for vehicle and N=4 for each drug group). On the afternoon of Days 1, 2 and 3, the vehicle, control or test drugs were administered (p.o.) to the ad libitum fed mice. On the morning of Day 4, the mice were weighed and food removed, but water was available ad libitum. Three hours later, a blood sample was collected and then the mice were given the fourth administration of drug or vehicle. Blood samples were collected again from the unanesthetized mice at 2 and 4 hrs after drug administration. The plasma was separated and levels of glucose in plasma was determined by the Abbott VP Analyzer.

For each mouse, the percent change of its plasma glucose level on Day 4 (mean of the 2 and 4 hr samples) from respective level before drug administration (Day 1 baseline sample) is determined as follows:

$$\frac{\text{mean of 2 and 4 hr samples (Day 4)}}{\text{Baseline Sample (Day 1)}} \times 100$$

Analysis of variance followed by Dunnett's multiple comparison (one-sided) will be used to estimate the degree of statistical significance of the difference between the vehicle control group and the individual drug-treated groups. A drug will be considered active, at the specific dosage administered, if the difference of the plasma glucose level has a p<0.05. The actual difference between the mean percent change of the vehicle and drug-treated groups is shown in Table 1.

The positive control, ciglitazone produces a 18 to 34% decrease in plasma glucose levels at 100 mg/kg/day×4 days, p.o.

TABLE 1

| Compound of Example No. | Dose mg/kg, p.o. | db/db data % Change glucose |
|---|---|---|
| 1 | 100 | −76 |
| 2 | 100 | −78 |
| 3 | 100 | −71 |
| 4 | 100 | −45 |
| 5 | 100 | −47 |
| 6 | 100 | −33 |
| 7 | 100 | −50 |
| 9 | 100 | −47 |
| 10 | 100 | −47 |
| 11 | 100 | −30 |
| 12 | 100 | −50 |
| 16 | 100 | −20 |
| 18 | 100 | −38 |
| 21 | 50 | −32 |
| 24 | 100 | −23 |
| 25 | 100 | −49 |

References:
1. Coleman, D. L. (1982) Diabetes-obesity syndromes in mice. Diabetes 31 (Suppl. 1); 1–6.
2. Tutwiler, G. F., T. Kirsch, and G. Bridi (1978). A pharmacologic profile of McN-3495 [N-(1-methyl-2-pyrrolidinylidene)-N'-phenyl-1-pyrrolidine-carboximidamide], a new, orally effective hypoglycemic agent. Diabetes 27:856–857.

3. Lee, S. M., G. Tutwiler, R. Bressler, and C. H. Kircher (1982). Metabolic control and prevention of nephropathy by 2-tetradecylglycidate in the diabetic mouse (db/db). Diabetes 31:12–18.
4. Chang, A. Y., B. W. Wyse, B. J. Gilchrist, T. Peterson, and R. Diani (1983) Ciglitazone, a new hypoglycemic agent. 1. Studies in ob/ob and db/db mice, diabetic Chinese hamsters, and normal and streptozocin-diabetic rats. Diabetes 32: 830–838.
5. Hosokawa, T., K. Ando, and G. Tamura (1985). An ascochlorin derivative, AS-6, reduces insulin resistance in the genetically obese diabetic mouse, db/db. Diabetes 34: 267–274.

Determination of Blood Glucose Lowering Effect in ob/ob mice

The non-insulin-dependent diabetic syndrome can be typically characterized by obesity, hyperglycemia, abnormal insulin secretion, hyperinsulinemia and insulin resistance. The genetically obese-hyperglycemic ob/ob mouse exhibits many of these metabolic abnormalities and is thought to be a useful media to search for hypoglycemic agents to treat NIDDM (Coleman, 1978)

Male or female ob/ob mice (C57B1/6J), ages 2 to 5 months (10 to 65 g), of a similar age are randomized according to plasma glucose into 4 groups of 10 mice. The mice are housed 5 per cage and are maintained on normal rodent chow with water ad libitum. The mice receive test compound daily. The test compound is suspended in 0.5 mL of 0.5% methyl cellulose and is administered by gavage (dissolved in drinking water) or admixed in the diet. The dose of compound given ranges from 2.5 to 200 mg/kg/day. Body weight of fed animals is measured at the beginning of each week and doses for the entire week are calculated using this weight and are expressed in terms of the active moiety of the compound. Control mice receive vehicle only.

On the morning of Days 4, 7 or 14 two drops of blood (approximately 50 µl) are collected into sodium fluoride containing tubes either from the tail vein or after decapitation. For those studies in which the compound is administered daily by gavage, the blood samples are collected four hour after compound administration. The plasma is isolated by centrifugation and the concentration of glucose is measured enzymatically on an Abbott V. P. Analyzer and the plasma concentration of insulin is determined by radioimmunoassay (Heding, 1972). For each mouse, the percentage change in plasma glucose on Day 4, 7 or 14 is calculated relative to the mean plasma glucose of the vehicle treated mice. Analysis of variance followed by Dunnett's Comparison Test (one tailed) is used to estimate the significant difference between the plasma glucose values from the control group and the individual compound treated groups. The results are presented in Table II.

The diabetic db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia (1). Furthermore, the db/db mouse will eventually develop some of the long-term complications that have been associated with diabetes mellitus (1). In spite of these commonalities, the acute administration of sulfonylureas (even at extremely high doses) will not reduce the hyperglycemia of the db/db mouse (2). The ability of a few other hypoglycemic agents to be effective in this species suggest that the other agents have mechanism of action which are different from that of the sulfonylureas (2,3,4,5). Such compounds, therefore, are more likely to be efficacious in the population of type II diabetic patients that do not respond to sulfonylurea therapy.

TABLE II

| Compound of Example No. | Dose mg/kg, p.o. | ob/ob data | |
|---|---|---|---|
| | | % Change glucose | % Change insulin |
| 4 | 100 | −39 | −82 |
| 6 | 100 | −39 | −76 |
| 7 | 100 | −30 | −75 |
| 10 | 100 | −36 | −28 |
| 22 | 100 | −32 | −91 |

References:
1. Brichard, S., Bailey, C. and Henquin, J.: Marked improvement of glucose homeostasis in diabetic ob/ob mice given oral vanadate. Diabetes 39: 1326–1332, 1990.
2. Chang, A., Wyse, B., Gilchrist, B., Peterson, T. and Diani, A.: Ciglitazone, a new hypoglycemic agent. I. Studies in ob/ob and db/db mice, diabetic Chinese hamsters, and normal and streptozoticin-induced diabetic rats. Diabetes 32: 830–838, 1983.
3. Coleman, D.: Obese and diabetes: Two mutant genes causing diabetes-obesity syndromes in mice. Diabetologia 14: 141–148, 1978.
4. Heding, L. G.: Determination of total serum insulin (IRI) in insulin-treated diabetic patients. Diabetologia 8: 260–266, 1972.

Pharmaceutical Composition

Based on the results of the pharmacological assay, the compounds of this invention are useful in the treatment of hyperglycemia in diabetes mellitus.

The compounds may be administered neat or with a pharmaceutical carrier to a mammal in need thereof. The pharmaceutical carrier may be solid or liquid and the active compound shall be a therapeutically effective amount.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. A dosage range of from 0.1 to 200 mg/kg/day is contemplated, with a preferred dosage of from 0.1 to 100 mg/kg/day. Due to uncertainty in relating laboratory mouse study data to other mammals, the degree of hyperglycemia, and the compound selected, the dosages used in the treatment of non-insulin dependent diabetes mellitus must be subjectively determined by a physician or veterinarian according to standard medical or veterinary practice.

What is claimed is:

1. A compound according to formula I below

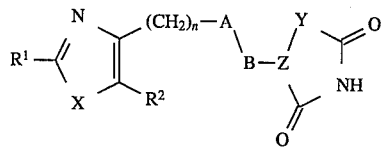

wherein:

$R^1$ is $C_1$–$C_6$ alkyl, $C_3$–$C_8$ cycloalkyl, thienyl, furyl, pyridyl,

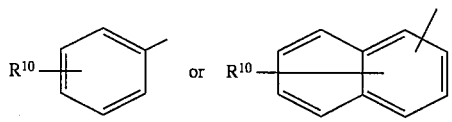

where $R^{10}$ is hydrogen, $C_1$–$C_6$ alkyl, fluorine, chlorine, bromine, iodine, $C_1$–$C_6$ alkyoxy, trifluoroalkyl or trifluoroalkoxy;

$R^2$ is hydrogen or $C_1$–$C_6$ alkyl;

X is O or S;

n is 1 or 2;

A is

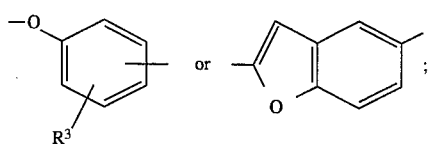

where $R^3$ is hydrogen, $C_1$–$C_6$ alkyl, halogen, $C_1$–$C_6$ alkoxy, trifluoroalkyl or trifluoroalkoxy;

B is

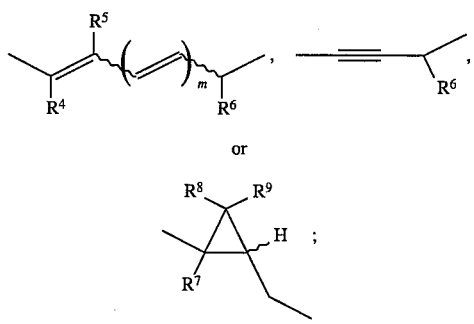

where $R^4$ is hydrogen, $C_1$–$C_6$ alkyl, allyl, $C_6$–$C_{10}$ aryl, $C_6$–$C_{10}$ aryl-$(CH_2)_{1-6}$—, fluorine, chlorine, bromine, iodine, trimethylsilyl or $C_3$–$C_8$ cycloalkyl;

$R^5$ is hydrogen, $C_1$–$C_6$ alkyl, $C_6$–$C_{10}$ aryl, or $C_6$–$C_{10}$ aryl-$(CH_2)_{1-6}$—;

m is 0, 1, or 2;

$R^6$ is hydrogen or $C_1$–$C_6$ alkyl;

$R^7$ is hydrogen or $C_1$–$C_6$ alkyl;

$R^8$ and $R^9$ are selected independently from hydrogen, $C_1$–$C_6$ alkyl, fluorine, chlorine, bromine, or iodine;

Y is O;

Z is N;

or a pharmaceutically acceptable salt thereof.

2. A compound according to claim 1 which has the formula Ia

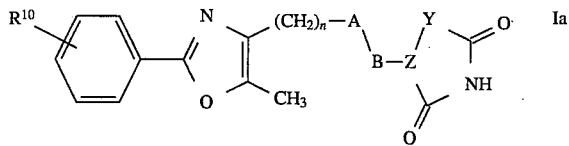

where:

$R^{10}$ is hydrogen, $C_1$–$C_6$ alkyl, fluorine, chlorine, bromine, iodine, $C_1$–$C_6$ alkoxy, trifluoroalkyl or trifluoroalkoxy;

n is 1 or 2;

A is

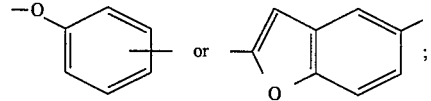

B is

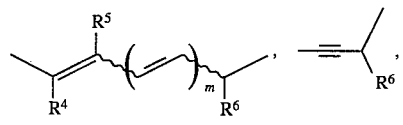

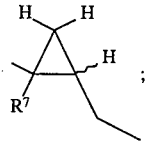

where m is 0, 1 or 2;

$R^4$, $R^5$, $R^6$, and $R^7$ are independently hydrogen or $C_1$–$C_6$ alkyl;

Y is O;
Z is N;
or a pharmaceutically acceptable salt thereof.

3. A compound according to claim 2 which has the formula Ib

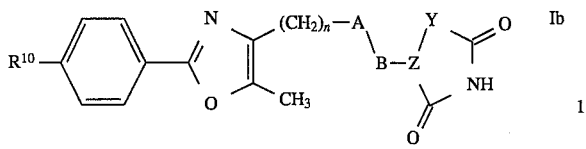

wherein:
$R^{10}$ is hydrogen, $CF_3-$, $CF_3O-$, $CF_3CH_2O-$ or $Cl-$;
n is 1 or 2;
A is

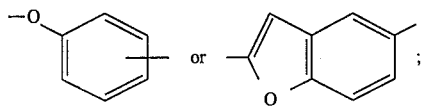

B is

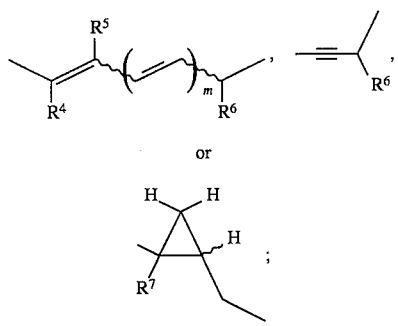

wherein
m is 0 or 1;
$R^4, R^5, R^6,$ and $R^7$ are independently hydrogen, methyl or ethyl;
Y is O;
Z is N;
or a pharmaceutically acceptable salt thereof.

4. A compound according to claim 3 which is selected from the group consisting of:
(E)-2-(3-{3-[5-methyl-2-(4-trifluoromethyl-phenyl)-oxazol-4-ylmethoxy]-phenyl}-pent-2-enyl)-[1,2,4]oxadiazolidine-3,5-dione,
(Z)-2-(3-{3-[5-methyl-2-(4-trifluoromethyl-phenyl)-oxazol-4-ylmethoxy]-phenyl}-pent-2-enyl)-[1,2,4]oxadiazolidine-3,5-dione,
2-(3-{3-[5-methyl-2-(4-trifluoromethyl-phenyl)-oxazol-4-ylmethyl]-phenyl}-but-2-enyl)-[1,2,4]oxadiazolidine-3,5-dione,
(E)-2-(3-{3-[5-methyl-2-(4-trifluoromethoxy-phenyl)-oxazol-4-ylmethoxy]-phenyl}-but-2-enyl)-[1,2,4]oxadiazolidine-3,5-dione,
(E)-2(3-{3-[5-methyl-2-(4-trifluoro-ethoxy-phenyl)-oxazol-4-ylmethoxy]-phenyl}-but-2-enyl)-[1,2,4]oxadiazolidine-3,5-dione,
(E)-2-{3-[3-(5-methyl-2-phenyl-oxazol-4-ylmethoxy)-phenyl]-but-2-enyl}-[1,2,4]oxadiazolidine-3,5-dione,
(Z)-2-{3-[3-(5-methyl-2-phenyl-oxazol-4-ylmethoxy]-phenyl]-but-2-enyl}-[1,2,4]oxadiazolidine-3,5-dione,
(E)-2-{3-[3-[2-(5-methyl-2-phenyl-oxazol-4-yl)-ethoxy]-phenyl}-but-2-enyl)-[1,2,4]oxadiazolidine-3,5-dione,
2-{3-[3-(5-methyl-2-phenyl-oxazol-4-ylmethoxy]-benzofuran-5-yl]-but-2-enyl}-[1,2,4]oxadiazolidine-3,5-dione,
(E)-2-(2-methyl-3-{4-[5-methyl-2-(4-trifluoromethyl-phenyl)-oxazol-4-ylmethoxy]-phenyl}-allyl)-[1,2,4]oxadiazolidine-3,5-dione,
(E)-2-(2-ethyl-3-{3-[5-methyl-2-(4-trifluoromethyl-phenyl)-oxazol-4-ylmethoxy]-phenyl}-allyl)-]1,2,4]oxadiazolidine-3,5-dione,
(E)-2-(1-methyl-3-{3-[5-methyl-2-(4-trifluoromethyl-phenyl)-oxazol-4-ylmethoxy]-phenyl}-allyl)-[1,2,4]oxadiazolidine-3,5-dione,
(E)-2-(3-{3-[2-(4-chloro-phenyl)-5-methyl-oxazol-4-ylmethoxy]-phenyl}-1-methyl-allyl)-[1,2,4]oxadiazolidine-3,5-dione,
(E)-2-(2-methyl-3-{3-[5-methyl-2-(4-trifluoromethyl-phenyl)-oxazol-4-ylmethoxy]-phenyl}-but-2-enyl)-[1,2,4]oxadiazolidine-3,5-dione,
(Z)-2-(2-methyl-3-{3-[5-methyl-2-(4-trifluoromethyl-phenyl)-oxazol-4-ylmethoxy]-phenyl}-but-2-enyl)-[1,2,4]oxadiazolidine-3,5-dione,
(E)-2-(1-methyl-3-{3-[5-methyl-2-(4-trifluoromethyl-phenyl)-oxazol-4-ylmethoxy]-phenyl}-but-2-enyl)-[1,2,4]oxadiazolidine-3,5-dione,
2-[3-(4-{4-[5-methyl-2-(4-trifluoromethyl-phenyl)-oxazol-4-ylmethoxy]-phenyl}-allyl)-[1,2,4]oxadiazolidine-3,5-dione,
(E)-2-(2-{3-[5-methyl-2-(4-trifluoromethyl-phenyl)-oxazol-4-ylmethoxy]- phenyl}-cyclopropylmethyl)-[1,2,4]oxadiazolidine-3,5-dione,
(E)-2-(2-methyl-2-{3-[5-methyl-2-(4-trifluoromethyl-phenyl)-oxazol-4-ylmethoxy]-phenyl}-cyclopropylmethyl)-[1,2,4]oxadiazolidine-3,5-dione,
(E,E)-2-{5-[3-(5-methyl-2-phenyl-oxazol-4-ylmethoxy]-phenyl}-hexa-2,4-dienyl)-[1,2,4]oxadiazolidine-3,5-dione,
(Z,E)-2-{5-[3-(5-methyl-2-phenyl-oxazol-4-ylmethoxyl]-phenyl}-hexa-2,4-dienyl)-[1,2,4]oxadiazolidine-3,5-dione,
2-[3-(4-{2-[5-methyl-2-(4-trifluoromethyl-phenyl-oxazol-4-yl]-ethoxy}-phenyl)-propyl-2-ynyl)-[1,2,4]oxadiazolidine-3,5-dione, and
2-{1-methyl-3-[3-(5-methyl-2-phenyl-oxazol-4-ylmethoxy)-phenyl]-propyl-2-ynyl}-]1,2,4]oxadiazolidine-3,5-dione.

5. A method of treating hyperglycemia of non-insulin dependent diabetes mellitus in mammals which comprises administration thereto of a therapeutically effective amount of a compound of formula I

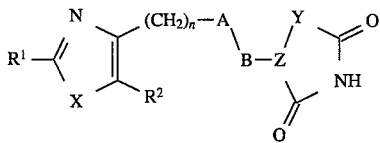

wherein:
$R^1$ is $C_1-C_6$alkyl, $C_3-C_8$cycloalkyl, thienyl, furyl, pyridyl,

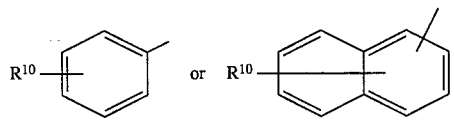

where $R^{10}$ is hydrogen, $C_1-C_6$ alkyl, fluorine, chlorine, bromine, iodine, $C_1-C_6$ alkyoxy, trifluoroalkyl or trifluoroalkoxy;

$R^2$ is hydrogen or $C_1$–$C_6$ alkyl;
X is O or S;
n is 1 or 2;
A is

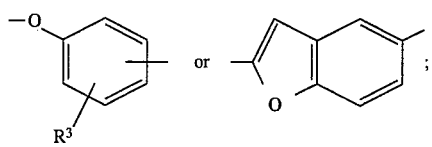

where $R^3$ is hydrogen, $C_1$–$C_6$ alkyl, halogen, $C_1$–$C_6$ alkoxy, trifluoroalkyl or trifluoroalkoxy;
B is

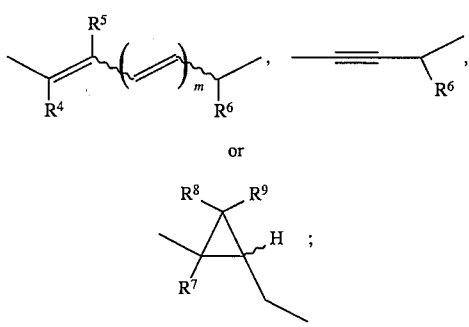

where:
$R^4$ is hydrogen, $C_1$–$C_6$ alkyl, allyl, $C_6$–$C_{10}$ aryl, $C_6$–$C_{10}$ aryl-$(CH_2)_{1-6}$—, fluorine, chlorine, bromine, iodine, trimethylsilyl or $C_3$–$C_8$ cycloalkyl;
$R^5$ is hydrogen, $C_1$–$C_6$ alkyl, $C_6$–$C_{10}$ aryl, or $C_6$–$C_{10}$ aryl-$(CH_2)_{1-6}$—;
m is 0, 1, or 2;
$R^6$ is hydrogen or $C_1$–$C_6$ alkyl;
$R^7$ is hydrogen or $C_1$–$C_6$ alkyl;
$R^8$ and $R^9$ are selected independently from hydrogen, $C_{-C6}$ alkyl, fluorine, chlorine, bromine, or iodine;
Y is O;
Z is N;
or a pharmaceutically acceptable salt thereof.

6. A method of treatment according to claim 5 wherein the compound used has the formula Ia

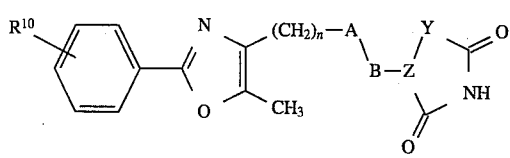

where:
$R^{10}$ is hydrogen, $C_1$–$C_6$ alkyl, fluorine, chlorine, bromine, iodine, $C_1$–$C_6$ alkoxy, trifluoroalkyl or trifluoroalkoxy;
n is 1 or 2;
A is

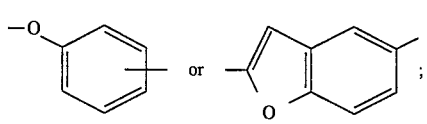

B is

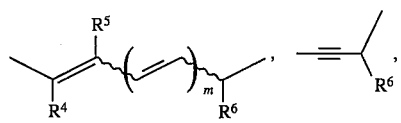

or

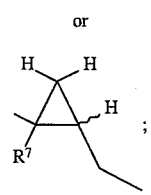

where
m is 0, 1 or 2;
$R^4$, $R^5$, $R^6$, and $R^7$ are independently hydrogen or $C_1$–$C_6$ alkyl;
Y is O;
Z is N;
or a pharmaceutically acceptable salt thereof.

7. A method of treatment according to claim 6 wherein the compound used has the formula Ib

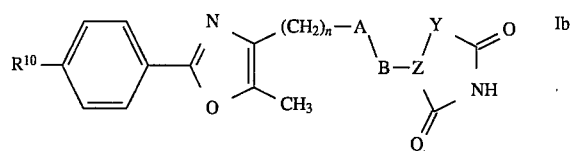

wherein:
$R^{10}$ is hydrogen, $CF_3$—, $CF_3O$—, $CF_3CH_2O$— or Cl—;
n is 1 or 2;
A is

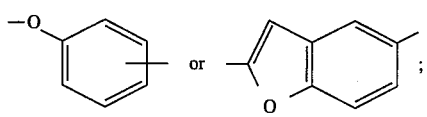

B is
wherein:
m is 0 or 1;
$R^4$, $R^5$, $R^6$, $R^7$ are independently hydrogen, methyl or ethyl;
Y is O;
Z is N;
or a pharmaceutically acceptable salt thereof.

8. A method of treatment according to claim 7 wherein the compound used is selected from the group consisting of:
(E)-2-(3-{3-[5-methyl-2-(4-trifluoromethyl-phenyl)-oxazol-4-ylmethoxy]-phenyl}-pent-2-enyl)-[1,2,4]oxadiazolidine-3,5-dione,
(Z)-2-(3-{3-[5-methyl-2-(4-trifluoromethyl-phenyl)-oxazol-4-ylmethoxy]-phenyl}-pent-2-enyl)-[1,2,4]oxadiazolidine-3,5-dione,
2-(3-{3-[5-methyl-2-(4-trifluoromethyl-phenyl)-oxazol-4-ylmethyl]-phenyl}-but-2-enyl)-[1,2,4]oxadiazolidine-3,5-dione,
(E)-2-(3-{3-[5-methyl-2-(4-trifluoromethoxy-phenyl)-oxazol-4-ylmethoxy]-phenyl}-but-2-enyl)-[1,2,4]oxadiazolidine-3,5-dione,
(E)-2-(3-{3-[5-methyl-2-(4-trifluoro-ethoxy-phenyl)-oxazol-4-ylmethoxy]-phenyl}-but-2-enyl)-[1,2,4]oxadiazolidine-3,5-dione, (E)-2-{3-[3-(5-methyl-2-phenyl-oxazol-4-ylmethoxy)-phenyl]-but-2-enyl}-[1,2,4]oxadiazolidine-3,5-dione,
(Z)-2-{3-[3-(5-methyl-2-phenyl-oxazol-4-ylmethoxy]-phenyl]-but-2-enyl}-[1,2,4]oxadiazolidine-3,5-dione,
(E)-2-{3-[3-[2-(5-methyl-2-phenyl-oxazol-4-yl)-ethoxy]-phenyl}-but-2-enyl)-[1,2,4]oxadiazolidine-3,5-dione,
2-{3-[3-(5-methyl-2-phenyl-oxazol-4-ylmethoxy]-benzofuran-5-yl]-but-2-enyl}-[1,2,4]oxadiazolidine-3,5-dione,
(E)-2-(2-methyl-3-{4-[5-methyl-2-(4-trifluoromethyl-phenyl)-oxazol-4-ylmethoxy]-phenyl}-allyl)-[1,2,4]oxadiazolidine-3,5-dione,
(E)-2-(2-ethyl-3-{3-[5-methyl-2-(4-trifluoromethyl-phenyl)-oxazol-4-ylmethoxy]-phenyl}-allyl)-[1,2,4]oxadiazolidine-3,5-dione,
(E)-2-(1-methyl-3-{3-[5-methyl-2-(4-trifluoromethyl-phenyl)-oxazol-4-ylmethoxy]-phenyl}-allyl)-[1,2,4]oxadiazolidine-3,5-dione,
(E)-2-(3-{3-[2-(4-chloro-phenyl)-5-methyl-oxazol-4-ylmethoxy]-phenyl}-1-methyl-allyl)-[1,2,4]oxadiazolidine-3,5-dione,
(E)-2-(2-methyl-3-{3-[5-methyl-2-(4-trifluoromethyl-phenyl)-oxazol-4-ylmethoxy]-phenyl}-but-2-enyl)-[1,2,4]oxadiazolidine-3,5-dione,
(Z)-2-(2-methyl-3-{3-[5-methyl-2-(4-trifluoromethyl-phenyl)-oxazol-4-ylmethoxy]-phenyl}-but-2-enyl)-[1,2,4]oxadiazolidine-3,5-dione,
(E)-2-(1-methyl-3-{3-[5-methyl-2-(4-trifluoromethyl-phenyl)-oxazol-4-ylmethoxy]-phenyl}-but-2-enyl)-[1,2,4]oxadiazolidine-3,5-dione,
2-[3-(4-{4-[5-methyl-2-(4-trifluoromethyl-phenyl)-oxazol-4-ylmethoxy]-phenyl}-allyl)-[1,2,4]oxadiazolidine-3,5-dione,
(E)-2-(2-{3-[5-methyl-2-(4-trifluoromethyl-phenyl)-oxazol-4-ylmethoxy]-phenyl}-cyclopropylmethyl)-[1,2,4]oxadiazolidine-3,5-dione,
(E)-2-(2-methyl-2-{3-[5-methyl-2-(4-trifluoromethyl-phenyl)-oxazol-4-ylmethoxy]-phenyl}-cyclopropylmethyl)-[1,2,4]oxadiazolidine-3,5-dione,
(E,E)-2-{5-[3-(5-methyl-2-phenyl-oxazol-4-ylmethoxy]-phenyl}-hexa-2,4-dienyl)-[1,2,4]oxadiazolidine-3,5-dione,
(Z,E)-2-{5-[3-(5-methyl-2-phenyl-oxazol-4-ylmethoxy]-phenyl}-hexa-2,4-dienyl)-[1,2,4]oxadiazolidine-3,5-dione,
2-[3-(4-{2-[5-methyl-2-(4-trifluoromethyl-phenyl-oxazol-4-yl]-ethoxy}-phenyl)-propyl-2-ynyl)-[1,2,4]oxadiazolidine-3,5-dione, and
2-{1-methyl-3-[3-(5-methyl-2-phenyl-oxazol-4-ylmethoxy)-phenyl]-propyl-2-ynyl}-[1,2,4]oxadiazolidine-3,5-dione.

9. A pharmaceutical composition for the treatment of hyperglycemia of non-insulin dependent diabetic mellitus in mammals comprising a pharmaceutical carrier and a therapeutically effective amount of a compound having the formula:

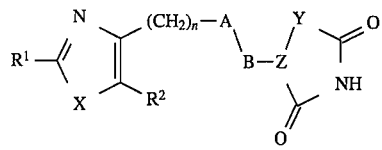 I wherein:

$R^1$ is $C_1$–$C_6$ alkyl, $C_3$–$C_8$ cycloalkyl, thienyl, furyl, pyridyl,

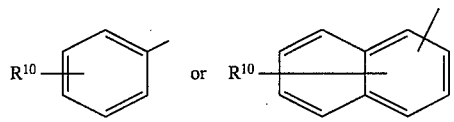

where $R^{10}$ is hydrogen, $C_1$–$C_6$ alkyl, fluorine, chlorine, bromine, iodine, $C_1$–$C_6$ alkyoxy, trifluoroalkyl or trifluoroalkoxy;

$R^2$ is hydrogen or $C_1$–$C_6$ alkyl;

X is O or S;

n is 1 or 2;

A is

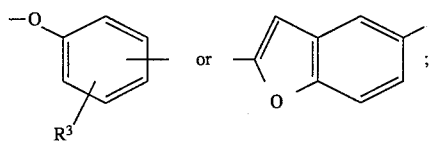

where $R^3$ is hydrogen, $C_1$–$C_6$ alkyl, halogen, $C_1$–$C_6$ alkoxy, trifluoroalkyl or trifluoroalkoxy;

B is

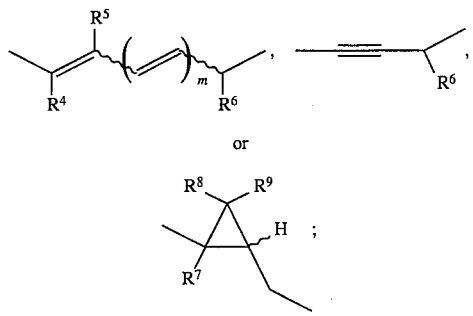

where $R^4$ is hydrogen, $C_1$–$C_6$ alkyl, allyl, $C_6$–$C_{10}$ aryl, $C_6$–$C_{10}$ aryl-$(CH_2)_{1-6}$—, fluorine, chlorine, bromine, iodine, trimethylsilyl or $C_3$–$C_8$ cycloalkyl;

$R^5$ is hydrogen, $C_1$–$C_6$ alkyl, $C_6$–$C_{10}$ aryl, or $C_6$–$C_{10}$ aryl-$(CH_2)_{1-6}$—;

m is 0, 1, or 2;

$R^6$ is hydrogen or $C_1$–$C_6$ alkyl;

$R^7$ is hydrogen or $C_1$–$C_6$ alkyl;

$R^8$ and $R^9$ are selected independently from hydrogen, $C_1$–$C_6$ alkyl, fluorine, chlorine, bromine, or iodine;

Y is O,

Z is N;

or a pharmaceutically acceptable salt thereof.